United States Patent [19]
Williams et al.

[11] Patent Number: 5,569,754
[45] Date of Patent: Oct. 29, 1996

[54] RNA IMPORT ELEMENTS FOR TRANSPORT INTO MITOCHONDRIA

[75] Inventors: R. Sanders Williams, Dallas; Kang Li, Irving, both of Tex.

[73] Assignee: Board of Regents, University of TX Systems, Austin, Tex.

[21] Appl. No.: 76,094

[22] Filed: Jun. 11, 1993

[51] Int. Cl.$^6$ .......................... C07H 21/02; C07H 21/04; C12N 15/70
[52] U.S. Cl. .......................... 536/23.5; 435/320.1
[58] Field of Search .................. 536/23.5; 435/320.1

[56] References Cited

PUBLICATIONS

Genbank Computer Alignment (2 pages).
Maniatis et al, "Molecular Cloning" (1989) pp. 16.5–16.17.
Annex et al., "Mitochondrial Biogenesis in Striated Muscles: Rapid Induction of Citrate Synthase mRNA by Nerve Stimulation," *Am. J. Physiol.*, 260 (Cell Physiol. 29):C266–C270, 1991.
Annex and Williams, "Mitochondrial DNA Structure and Expression in Specialized Subtypes of Mammalian Striated Muscle," *Mol. Cell. Biol.*, 10(11):5671–5678, 1990.
Baldacci et al., "tRNA in Mitochondria from *Saccharomyces Cerevisiae* Grown in Different Physiological Conditions: Hybridization on Mitochondrial DNA Fragments and Import of Cytoplasmic Species," *The Genetic Function of Mitochondrial DNA*, C. Saccone and A. M. Kroon, Eds., pp. 305–312, 1976.
Di Monte, Donato A., "Mitochondrial DNA and Parkinson's Disease," *Neurology*, 41(suppl. 2):38–42, 1991.
Ellis, R. John, "Molecular Chaperones," *Annu. Rev. Biochem.*, 60:321–347, 1991.
Firgaira et al., "RNA Required for Import of Precursor Proteins into Mitochondria," *Science*, 236:1319–1322, 1984.
Grossman, Lawrence I., "Invited Editorial: Mitochondrial DNA in Sickness and in Health," *Am. J. Hum. Genet.*, 46:415–417, 1990.
Harding, A. E., "Neurological Disease and Mitochondrial Genes," *Trends Neurosci.*, 14(4):132–138, 1991.
Harlan, William R., and Williams, R. Sanders, "Activity-–Induced Adaptations in Skeletal Muscles of Iron–Deficient Rabbits," *J. Appl. Physiol.*, 65(2):782–787, 1988.
Hattori et al., "Age–Dependent Increase in Deleted Mitochondrial DNA in the Human Heart: Possible Contributory Factor to Presbycardia," *Am. Heart J.*, 121:1735–1742, 1991.
Kraus et al., "Interactions Between Sustained Contractile Activity and β–Adrenergic Receptors in Regulation of Gene Expression in Skeletal Muscles," *Am. J. Physiol.* 256(Cell Physiol. 25):C506–C514, 1989.
Lander, Eric S., and Lodish, Harvey, "Mitochondrial Diseases: Gene Mapping and Gene Therapy," *Cell*, 61:925–926, 1990.
Linnane et al., "Mitochondrial DNA Mutations as an Important Contributor to Ageing and Degenerative Diseases," *The Lancet*, pp. 642–645, 1989.
Maréchal–Drouard et al., "Import of Several tRNAs from the Cytoplasm into the Mitochondria in Bean *Phaseolus vulgaris*," *Nucl. Acids Res.*, 16(11):4777–4788, 1988.
Ozawa et al., "Patients with Idiopathic Cardiomyopathy Belong to the Same Mitochondrial DNA Gene Family of Parkinson's Disease and Mitochondrial Encephalomyopathy," *Biochem. Biophys. Res. Commun.*, 177(1):518–525, 1991.
Söderlind et al., "Chaperonin Assisted Phage Display of Antibody Fragments on Filamentous Bacteriophages," *Bio/Technology*, 11:503–507, 1993.
Topper, James N., and Clayton, David A., "Characterization of Human MRP/Th RNA and Its Nuclear Gene: Full Length MRP/Th RNA is an Active Endoribonuclease When Assembled as an RNP," *Nucl. Acids Res.*, 18(4):793–799, 1990.
Trounce et al., "Decline in Skeletal Muscle Mitochondrial Respiratory Chain Function: Possible Factor in Ageing," *The Lancet*, pp. 637–639, Mar. 25, 1989.
Vestweber, Dietmar, and Schatz, Gottfried, "DNA–Protein Conjugates Can Enter Mitochondria via the Protein Import Pathway," *Nature*, 338:170–172, 1989.
Williams, R. Sanders, "Genetic Mechanisms That Determine Oxidative Capacity of Striated Muscles. Control of Gene Transcription," *Circulation*, 82(2):319–331, 1990.
Williams, R. Sanders, "Mitochondrial Gene Expression in Mammalian Striated Muscle. Evidence That Variation in Gene Dosage is the Major Regulatory Event," *J. Biol. Chem.*, 261(26):12390–12394, 1986.
Williams et al., "Adaptation of Skeletal Muscle to Increased Contractile Activity," *J. Biol. Chem.*, 262(6):2764–2767, 1987.
Williams et al., "Regulation of Nuclear and Mitochondrial Gene Expression by Contractile Activity in Skeletal Muscle," *J. Biol. Chem.*, 261(1):376–380, 1986.
Williams, R. Sanders, and Harlan, William, "Effects of Inhibition of Mitochondrial Protein Synthesis in Skeletal Muscle," *Am. J. Physiol.*, 253(Cell Physiol. 22):C866–C871, 1987.
Dialog Search Report dated Feb. 4, 1992.
Chang and Clayton, "Mouse RNAase MRP RNA Is Encoded by a Nuclear Gene and Contains a Decamer Sequence Complementary to a Conserved Region of Mitochondrial RNA Substrate", *Cell*, 56:131–139, 1989.

(List continued on next page.)

Primary Examiner—W. Gary Jones
Assistant Examiner—Eggerton Campbell
Attorney, Agent, or Firm—Arnold, White & Durkee

[57] ABSTRACT

The invention relates to small RNAs encoded within the nucleus of mammalian cells that specifically import to the mitochondria. The RNAs bind to several nucleolar peptides and thus provide potential carriers for import of biological molecules, including metabolites and proteins, into the mitochondrial compartment. Mitochondrial dysfunction in several maternally inherited human diseases may be correctable employing linkage of mitochondrial import signal to mitochondrial tRNA sequences expressed from nuclear transgenes without requirement for direct genetic transformation of mitochondria.

8 Claims, 21 Drawing Sheets

OTHER PUBLICATIONS

Kiss and Filipowicz, "Evidence Against a Mitochondrial Location of the 7–2/MRP RNA in Mammalian Cells", *Cell,* 70:11–20.

Li, K., et al., "Subcellular Partitioning of MRP RNA Assessed by Ultrastructural and Biochemical Analysis", *The Journal of Cell Biology,* 124(6):871–882, 1994.

Topper and Clayton, "Secondary Structure of the RNA Component of a Nuclear/Mitochondrial Ribonucleoprotein", *The Journal of Biological Chemistry,* 265(22):13254–13262, 1990.

International Search Report, PCT/US94/06132, mailed Oct. 27, 1994.

wt-
del- 1 2 3 4 5

— 16s

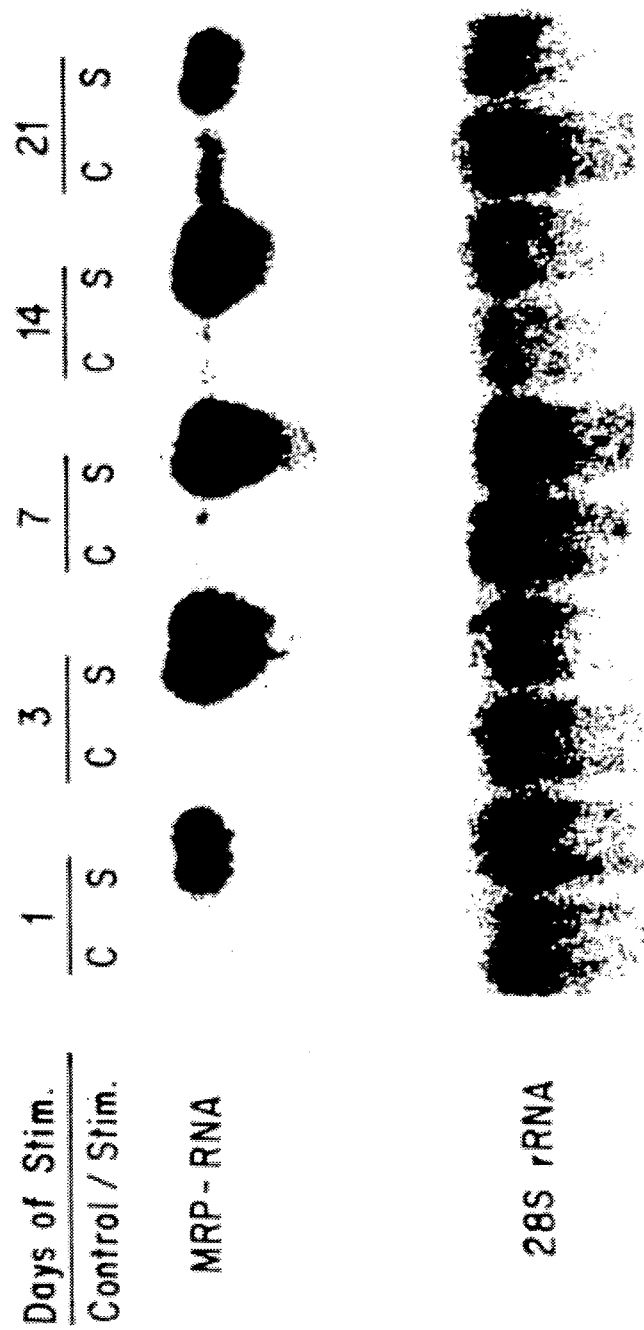

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 100 base pairs
        ( B ) TYPE: nucleic acid (C) STRANDEDNESS: double
(D) TOPOLOGY: linear (i i) MOLECULE TYPE: DNA (x i) SEQUENCE DESCRIPTION: SEQ ID NO:1:

GCGTGCACAC GCGCGTAGAC TTCCCCCGCA AGTCACTCGT TAGCCCGCCA AGAAGCGACC    60

CCTCCGGGGC GAGCTGAGCG GCGTGGCGCG GGGGCGTCAT    100

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: RNA (x i) SEQUENCE DESCRIPTION: SEQ ID NO:2:

GACUUCCCCC GCAAGUC    17

(2) INFORMATION FOR SEQ ID NO:3:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: RNA (x i) SEQUENCE DESCRIPTION: SEQ ID NO:3:

CCGCCAAGAA GCG    13

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:4:

GAATGAGATC TGTGGTTGGT GCG    23

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:5:

CATGTCCCTC GTATGTAGCC TAG    23

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:6:

GAGAATGAGC CCCGTGTGGT TG    22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

GGTCTAAACC CAGCTCACGT TC    22

( 2 ) INFORMATION FOR SEQ ID NO:8:

( i ) SEQUENCE CHARACTERISTICS:
        ( A ) LENGTH: 101 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:8:

ACGTGCATAC GCACGTAGAC ATTCCCCGCT TCCCACTCCA AAGTCCGCCA AGAAGCGTAT    60

CCCGCTGAGC GGCGTGGCGC GGGGGCGTCA TCCGTCAGCT C    101

( 2 ) INFORMATION FOR SEQ ID NO:9:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:9:

ACTTCCCCCG CAAGTCACTC GTTAGCCCGC CAAGAAGCGA CCCCTCCGGG GCGAGCTG    58

RNA IMPORT ELEMENTS FOR TRANSPORT INTO MITOCHONDRIA

The United States Government has certain rights in the invention in accordance with grants HL-35639 and HL06296 awarded by the National Institutes of Health.

BACKGROUND OF THE INVENTION

1. Field of the Invention

The present invention relates generally to the field of molecular biology and to its application in the utilization of nucleic acid transcripts which import biological molecules from the cell cytoplasm into mitochondria. The invention also concerns vectors incorporating DNA encoding the transcripts and various peptide/RNA mitochondrial import complexes. The nucleic acid segments copy RNA molecules which can transport additional RNA sequences, peptides or DNA molecules into the mitochondrial matrix. Also disclosed are methods of gene therapy directed at mitochondrial gene defects.

2. Description of Related Art

Mitochondria have been recognized as having a role in certain diseases and may be directly related to some aspects of the ageing process. An increased understanding of the function of mitochondrial genes in relation to the nuclear genes has therefore been the subject of much interest and research.

Current views of mitochondria hold that mitochondria import most small molecules and proteins from the cytoplasm. There is some evidence that RNA may also be imported, although the mechanism is not clear (Vestweber and Schatz, 1989).

The mammalian mitochondrial genome is different from nuclear genes in both structure and function. The human mitochondrial genome is small and economically packaged, lacking the large intervening sequences of non-coding DNA (introns) that constitute most of the nuclear genome. Mitochondrial amino acids are determined by a different genetic code than those in nuclear genes. Numerous other differences exist between nuclear and mitochondrial genes; for example, the monocistronic transcription from individual promoters and the extensive post transcriptional cleavage and ligation steps. Characteristic of mRNA synthesis directed by nuclear genes mitochondrial DNA is transcribed as a single polycistronic message subsequently cleaved to produce individual transfer, ribosomal and messenger RNA transcripts.

Mitochondrial biogenesis requires the participation of two distinct genetic compartments: the nuclear genome that contributes the vast majority of mitochondrial proteins and the mitochondrial genome that contributes 13 protein subunits to inter membrane enzymes of the respiratory chain (Anderson et al., 1981; Bibb et al., 1981). With the exception of two ribosomal RNA subunits and a complete set of tRNA species, the gene products necessary for replication transcription and translation of mitochondrial genes in cells of higher eukaryotes are derived entirely from the nucleus (Kruse et al., 1989; Parisi and Clayton, 1991; Attardi and Schatz, 1988). The set of nuclear genes required for replication and expression of the mitochondrial genome appears to include not only protein coding genes but loci that encode small RNA transcripts. Nuclear-encoded tRNAs have been observed in mitochondria from lower eukaryotes (Mottran et al., 1991; Nagley, 1989) and mitochondrial RNaseP in mammalian cells may include a nuclear encoded RNA subunit (Doersen et al., 1985). Even more definitive evidence for the participation of small RNA transcripts of nuclear origin in essential mitochondrial functions lies in the discovery of a mammalian RNase MRP that is presumed to generate primers for mitochondrial DNA replication (Chang and Clayton, 1987a; 1987b). This enzyme requires an RNA subunit (MRP-RNA) encoded by a single copy nuclear gene that is highly conserved among the mammalian species (Chang and Clayton, 1989; Yuan et al., 1989; Gold et al., 1989).

Most of the total cellular pool of MRP-RNA is localized within nucleoli (Reimer et al., 1988) but a small fraction of MRP-RNA partitions to mitochondria (Chang and Clayton, 1987b). The nuclear and cytoplasmic enzymes associated with MRP RNA exhibit some distinctions in RNase activity (Karwan et al., 1991). The mitochondrial RNase MRP cleaves a mitochondrial RNA substrate (transcribed in vitro) at a unique site between conserved sequence blocks (CSB) II and III. Mutations in CSB II and III severely inhibit the cleavage (Bennett and Clayton, 1990). In contrast, nuclear RNase MRP cleaves the same RNA substrate in multiple sites. Variations in the enzymatic properties of mitochondrial and nuclear RNases that contain identical MRP-RNA subunits are attributable to differences in apoprotein components (Karwan et al., 1991).

The mitochondrial inner membrane is impermeable to charged molecules so that transport of metabolites and proteins is accomplished by specialized carriers for small molecules (Aquila et al., 1987) and by an elaborate import apparatus for proteins (Sollner et al., 1991; Manning-Krieg et al., 1991). The partitioning of MRP-RNA to the mitochondrial compartment after transcription within the nucleus suggests the existence of a pathway by which RNA transcripts exit the nucleus and are imported across both the outer and inner mitochondrial membranes to the site of holoenzyme assembly within the mitochondrial matrix. However, such an import pathway has not been elucidated, nor has there been identification of sequence-specific targeting that might provide a signal for mitochondrial import.

The variable proportion of mutant mitochondrial genomes per cell results in cells with a range of bioenergetic capacities. Moreover, the expression of the whole genome is essential for the maintenance of mitochondrial bioenergetic function. Despite this knowledge of mitochondrial gene structure and of the biochemical steps involved in mitochondrial gene expression, relatively little is known about processes that regulate the expression of mammalian mitochondrial genes.

Mitochondrial function has been the subject of numerous studies, both in energy regulation and as a source of DNA mutations that may contribute to aging and degenerative diseases. Age dependent increases in deleted mitochondrial DNA, for example, have been found in the human heart (Hattori et al., 1991). Certain diseases such as Parkinson's disease, appear to be closely related to aging. Deletions in aging heart tissue are similar to those found in some Parkinson's patients and it has been speculated that some factors that accelerate mitochondrial DNA mutations may contribute to both Parkinson's disease and cardiomyopathy.

Other diseases and conditions may also be associated with defects in mitochondrial DNA. These include Kearns-Sayre syndrome and retinitis pigmentosa, ataxia, seizures, dementia and proximal muscle weakness (Grossman, 1990). A single base change in human mitochondrial DNA has been correlated with the appearance of Leber Hereditary Optic Neuropathy (LHON). LHON is a form of central optic nerve death resulting in blindness in affected individuals at a relatively early age, typically in their early twenties.

The identification of a region of RNA that may serve as a mitochondrial targeting signal has potential clinical significance. Several maternally inherited human diseases are associated with deletions and point mutations in the mitochondrial genome (Holt et al., 1988; Wallace et al., 1988; Shoffner et al., 1990; Goto et al., 1990). For example, myoclonic epilepsy and ragged-red fiber disease (MERRF) and mitochondrial myopathy, encephalomyopathy, lactic acidosis, and strokelike episodes (MELAS) are attributable to single base substitutions in tRNA$^{Lys}$ and tRNA$^{Leu}$, respectively (Shoffner et al., 1990; Goto et al., 1990). The tRNA$^{Lys}$ mutation causes a general reduction in mitochondrial protein synthesis (Chomyn et al., 1991).

Prospects for gene therapy directed at mitochondrial gene defects are limited currently by the absence of methods for efficient introduction of foreign genetic material into mitochondria (discussed by Lander and Lodish, 1990). Mitochondrial dysfunction in cells of MERRF and MELAS patients may be correctable by linkage of a mitochondrial import signal to mitochondrial tRNA sequences expressed from nuclear trans-genes, without a requirement for direct genetic transformation of mitochondria.

SUMMARY OF THE INVENTION

The present invention seeks to address the problems and needs inherent in the prior art by elucidating RNA transcripts with unique mitochondrial transport functions. Identification of the novel RNA transcripts provides routes to novel therapies directed toward mitochondrial gene defects and dysfunction. The invention also includes novel peptide/nucleic acid compositions, RNA transport elements and methods of introducing genetic material into the mitochondrion.

The inventors have discovered MRP-RNA transcripts that import to the mitochondria. Specific regions of a MRP-RNA gene have been identified that are essential for import of small RNA transcripts into the mitochondria but at the same time are dispensable for transcription, nuclear partitioning or stability of the transcript in the cytoplasmic compartment. The inventors have shown that specific sequence elements are required to direct RNA to a mitochondrial import pathway.

It has been found that transcriptional control elements sufficient to direct MRP gene transcription reside within the proximal 700 bp of 5' flanking DNA. This upstream region of mouse MRP-RNA gene includes an array of regulatory motifs similar to those of the U6 and 7SK RNA genes. Deletion of either the putative distal or proximal sequence elements from the MRP-RNA promoter eliminates transcription. This places the MRP-RNA gene with U6 and 7SK RNA as a member of the set of POLIII transcribed genes controlled by upstream sequences without a requirement for internal elements governing transcription.

In particular, the inventors have isolated an RNA transcript which functions as a mitochondrial import carrier. The transcript is encoded within the mid-portion of mammalian MRP-RNA gene between coding region nt100 and nt200 (SEQ ID NO: 1, mouse; SEQ ID NO: 8, human); more particularly, between coding region nt118 and 175 (SEQ ID NO: 9). Part of this region, namely the region between nt144 and nt156 (SEQ ID NO: 3) includes an evolutionary conserved sequence within a flexible base pairing region and a stable stem loop. The stem loop is preserved in all forms of MRP-RNA that import efficiently into mitochondria. These structural features of the RNA segment between nt118 and nt175 (SEQ ID NO: 9) of MP-RNA may provide a recognition signal for proteins that service carriers in the pathway between the nucleus and the mitochondrial matrix. Therefore, mitochondrial carriers are likely not limited to transcripts defined by the complete region between nt118 and nt175 (SEQ ID NO: 9), but may include shorter regions. Such regions are expected to include the highly conserved sequence between nt144 to nt156, as well as some structural features enabling the formation of a stable stem loop. Thus RNA transcripts comprising relatively short regions of at least 10 base pairs or longer regions of 20, 30, 40 base pairs up to 100 base pairs or longer which include this conserved sequence may be expected to function as carriers between the nucleus and the mitochondria.

A further aspect of the invention is the discovery that particular mitochondrial import RNA transcripts are stabilized by binding with nucleolar proteins. The inventors have discovered that reduced stability occurs in some mutant RNA transcripts. Such unstable transcripts lack the region of MRP-RNA containing the binding site for To/Th antigen. It is known that To/Th antigen has high affinity for MRP-RNA and apparently confers stability upon binding with the RNA. Impaired mitochondrial partitioning of certain MRPF mutants may therefore be attributable to failure of the transcript to be recognized by a protein carrier of a mitochondrial import apparatus and lability may be due to defective binding of a protein that stabilizes the transcript within the nucleolar compartment. Binding sites for protein stabilization sequences could be engineered into import RNA sequences.

In further embodiments, the present invention contemplates compositions comprising nucleic acid segments, i.e., DNA segments or RNA segments, which have a sequence in accordance with or complementary to SEQ ID NO: 1 or 8 or to segments of SEQ ID NO: 1 or 8 which represents part of MRP-RNA gene. Certain nucleic acid segments comprising the sequence between coding region nt100 and nt200 are useful as DNA probes of the MRP-RNA gene. Probes selected from segments of the MRP-RNA gene between nt100 and nt200 are useful for identifying specific regions of that coding region. One may, for example, wish to identify shorter or longer regions of targeting RNA transcripts in order to modify import properties. One generally wishes to select probes at least 10 base pairs in length up to the length of the mitochondrial import RNA transport region encoded within the mid-portion of the mammalian MRP-RNA gene which is 100 base pairs in length.

In addition to utility as probes for isolating and identifying regions of RNA import transcripts, DNA segments may be employed as primers to amplify particular regions of interest of the MRP-RNA gene. In preferred embodiments, one may employ different oligonucleotide primers for such amplifications. Deletion mutants, for example, may be generated by PCR primer-guided synthesis. DNA sequences complementary to isolated RNA transcripts are readily generated based on techniques known to those in the art. Typically employed primers are from 10 to 30 base pairs in length, although most preferable lengths are 15–25 base pairs.

Further aspects of the invention contemplate stabilized complexes between the disclosed RNA transcripts and cellular peptides. Such peptides will bind to the RNA to confer stability. Cellular peptides may include nucleoplasmins, chaperonins, heat shock protein 70, signal recognition particles, α-lytic factor prosequence, ubiquitinated ribosomal proteins, trigger factor, sec B protein, Pap D protein or other unrelated classes of proteins that act as molecular chaperones (Ellis and van der Yies, 1991). A preferred complex is a peptide To/Th antigen bound to the MRP-RNA transcript according to SEQ ID NO: 1 or 8.

Recombinant vectors and recombinant cells transformed with the recombinant vectors are also contemplated as part of the present invention. Such vectors will include DNA segments which are transcribable to the disclosed mitochondrial import transcript. A preferred DNA encodes the mitochondrial import RNA transcript encoded within the midportion of mammalian MRP-RNA gene between coding region nt100 and nt200. Vectors may be prepared by any of numerous means well known to those of skill in the art. These vectors will include an appropriate signal sequence for mitochondrial import and transcriptional control elements appropriate to the type of cell one desires to transform or transfect.

Suitable cell hosts include prokaryotic and eukaryotic cells. Preferred host cells are myoblast cells, such as C2C12 mouse myoblast cells. Prokaryotic cells are contemplated to be useful also; for example, one may employ E. coli or Salmonella cells transformed with an appropriate vector designed for expression in such prokaryotes. Convenient sources of commercially available vectors into which DNA may be cloned for transfection or transcription into appropriate cells include Strategene (La Jolla, Calif.), Mo Bi Tec (Wagenstieg, Göttingen, FRG).

The inventors have identified particular RNA transcripts that direct import into the mitochondria. This discovery provides the basis for the disclosed method of importing biological molecules into the mitochondria. The method includes facilitating an association between an RNA import transcript and a biological molecule so that a complex is formed and introducing the complex into a targeted cell. The biological molecule may be a DNA, other RNA sequences or a polypeptide. In preferred embodiments, the transport RNA has the 58 bp sequence within SEQ ID NO: 1 or 8 which corresponds to nt118–nt175 in the MRP-RNA mammalian gene. Peptide RNA complexes are contemplated to be those which the peptide binds to the RNA transport molecule.

RNA transport transcripts may be designed such that particular peptides specifically bind, thus not limiting binding to nucleolar peptides. Such a method is contemplated to be useful in the treatment of human diseases associated with deletions and point mutations in the mitochondrial genome. Diseases such as myoclonic epilepsy, ragged red fiber disease, mitochondrial myopathy and encephalomyopathy, lactic acidosis and stroke-like episodes are attributable to single-base substitutions in tRNA lysine and tRNA leucine. The tRNA lysine mutation causes a general reduction in mitochondrial protein synthesis. Mitochondrial dysfunction in cells of these patients may be correctable by linking a mitochondrial import signal to mitochondrial tRNA sequences expressed from nuclear transgenes, thereby eliminating a requirement for direct genetic transformation of mitochondria.

The present invention also contemplates insertion of foreign nucleic acids into mitochondria. Thus, one combines a DNA segment which is complementary to a desired DNA with an RNA mitochondrial import transcript which may be selected for example from SEQ ID NO: 1 or 8 or from segments of DNA in accordance with SEQ ID NO: 1 or 8, preferably segments including the loop region between nt144–nt156. The complex is then introduced into a targeted cell by established methods; for example, by calcium phosphate co-precipation, liposomes or viral vectors.

The present invention also embodies kits for use in detecting MRP-RNA transcripts. Kits for use in both Southern and Northern blotting are contemplated. Such kits will generally comprise a first container which includes one or more nucleic acid probes having a sequence in accordance with the sequences of the nucleic acid probes represented by SEQ ID NO: 4, SEQ ID NO: 5 and SEQ ID NO: 6 and a second container comprising one or more unrelated nucleic acids for use as a control. In preferred embodiments, such kits will include all such nucleic acid probes or segments.

Kits including nucleic acid sequences in accordance with SEQ ID NO: 1 or 8 or segments of Seq ID NO: 1 or 8 which include nt144–nt156 (SEQ ID NO: 3) are also contemplated. Such segments will be useful for targeting selected nucleic acids to the mitochondria. Modified sequences, designed to bind specific proteins may also be included, as may vectors into which selected sequences for coding a specific polypeptide may be inserted.

BRIEF DESCRIPTION OF THE DRAWINGS

FIG. 3a) is an RNA blot hybridized with MRP probe 1, which detects all of the mutant forms of MRP-RNA but not the endogenous gene product: Lane 1, 3 µl of 1,000-fold dilution of RNA transcribed in vitro from pMRP-A (positive control). Lane 2, 5 µg of total RNA from mock transfection. Lane 3–5, 5 µg of total RNA each from cells transfected with pMRP-A, pMRP-D and pMRP-F, respectively. FIG. 3b) RNA blot hybridized with MRP probe 2, which detects the endogenous gene product and transcripts of pMRP-A and pMRP-B, as shown: Lane 1, 5 µg of total RNA from mock transfection. Lane 2, in vitro transcript of pMRP-A. Lane 3, 5 µg of total RNA from cells transfected with pMRP-B. wt: endogenous MRP-RNA. del, deleted form of MRP-RNA. FIG. 3c) Plasmid extraction from the transfected cells. Lane 1, mock transfection. Lane 2–5, plasmids pMRP-A, pMRP-D, pMRP-F and pMRP-B from transfected cells. One half of the preparation (representing an equal number of cells) was loaded in each lane.

FIG. 4a: transcripts of pMRP-A detected by probe 1. FIG. 4b: endogenous MRP-RNA detected by probe 3. FIG. 4c: U1 RNA (nuclear marker). FIG. 4d: 16S mitochondrial ribosomal RNA (mitochondrial marker). FIG. 4e: 28s ribosomal RNA (cytoplasmic marker), Lane 1, total cellular RNA. Lane 2, in vitro transcript of pMRP-A. Lanes 3, 4 and 5, mitochondrial RNAs isolated after 1st, 2nd and 3rd fractionation steps, respectively (see FIG. 2). Lanes 2–4 of panel e correspond to lanes 3–5 in the other panels. Five µg of total or mitochondrial RNA were loaded in each lane in panels a–c, and 2 µg were loaded in panels d–e. FIG. 4f:

Profile of mitochondrial partition of MRP-RNAs versus U1 RNA. Densitometric quantification of hybridization signals was obtained from two independent transfection experiments, and the ratio of endogenous MRP-RNA (filled columns) or transcripts derived from pMRP-A (hatched columns) was calculated as a ratio (vertical axis) relative to the U1 RNA signal in the 1st, 2nd and 3rd sequential mitochondrial purification steps.

Figure 5A:
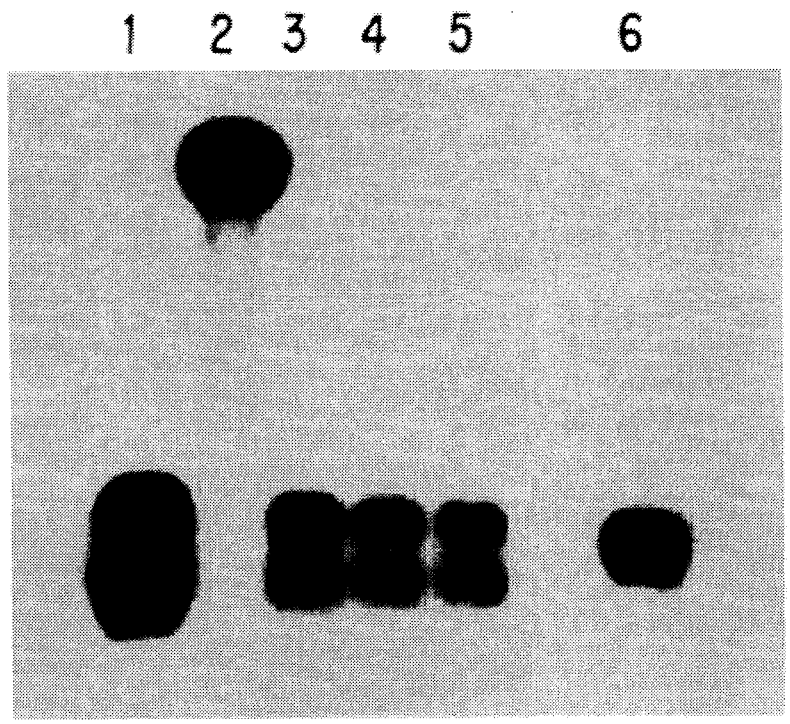
Figure 5B:
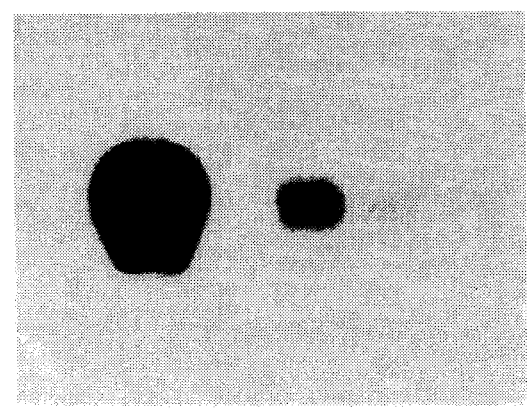
Figure 5C:

FIGS. 5A–C are Northern blot hybridization showing mitochondrial partitioning of transcripts derived from pMRP-B. FIG. 5a shows transcripts of both endogenous MRP-RNA and pMRP-B detected by probe 2. Wild type and deleted forms of MRP-RNA are indicated by wt and del, respectively. FIG. 5b shows U1 RNA (nuclear marker) FIG. 5c is 16S mitochondrial ribosomal RNA (mitochondrial marker): lane 1, total cellular RNA: lane 2, in vitro transcript of pMRP-B: lanes 3, 4 and 5, mitochondrial RNAs isolated after 1st, 2nd and 3rd fractionation steps, respectively (see FIG. 2): lane 6, total RNA from mock transfection. Five µg of total or mitochondrial RNA were loaded in each lane in panels a and b, and 2 µg were loaded in panel c.

Figure 6A:
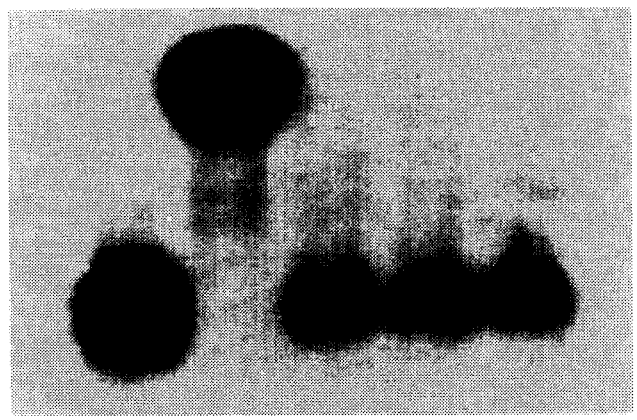
Figure 6B:
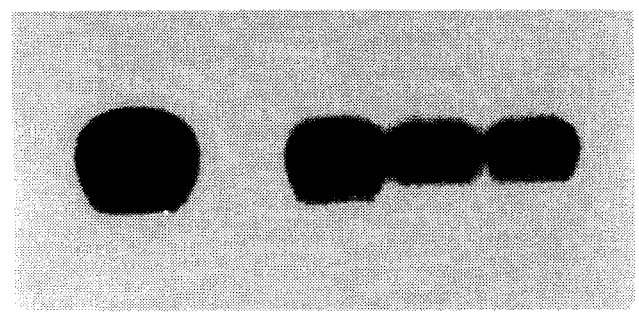
Figure 6C:
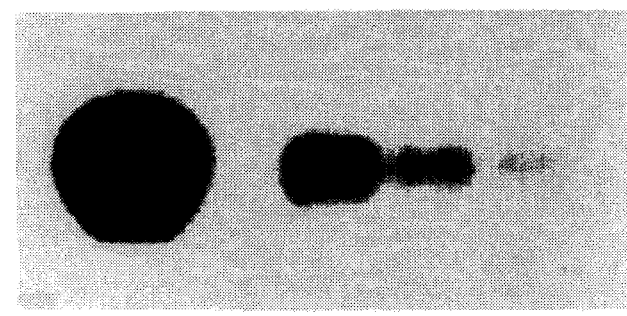
Figure 6D:
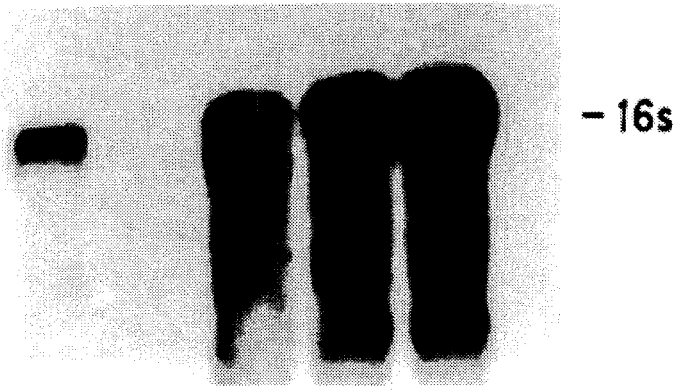

FIGS. 6A–D are Northern blot hybridizations showing mitochondrial partitioning of transcripts derived from pMRP-D. FIG. 6a shows transcripts of pMRP-D detected by probe 1; FIG. 6b shows endogenous MRP-RNA detected by probe 3; FIG. 6c is U1 RNA (nuclear marker); FIG. 6d is 16S mitochondrial ribosomal RNA (mitochondrial marker): lane 1, total cellular RNA; lane 2, in vitro transcript of pMRP-D; lanes 3, 4 and 5, mitochondrial RNAs isolated after 1st, 2nd and 3rd fractionation steps, respectively (see FIG. 2). Five µg of total or mitochondrial RNA were loaded in each lane in panels a–c, and 2 µg were loaded in panel d.

Figure 7A:
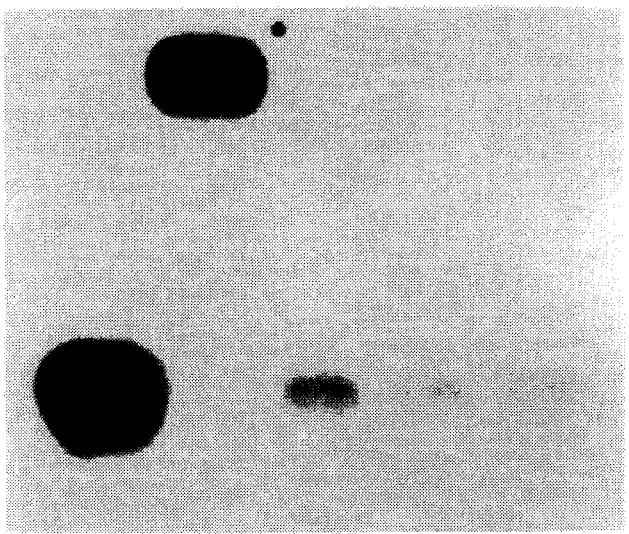
Figure 7B:
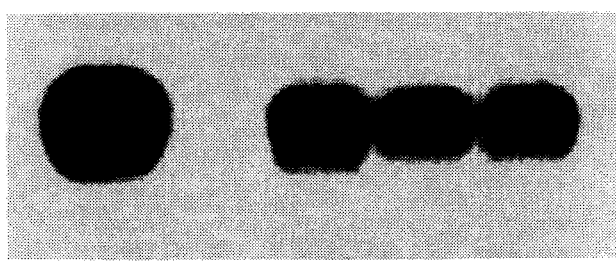
Figure 7C:
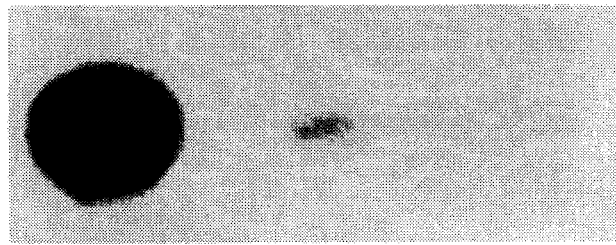
Figure 7D:
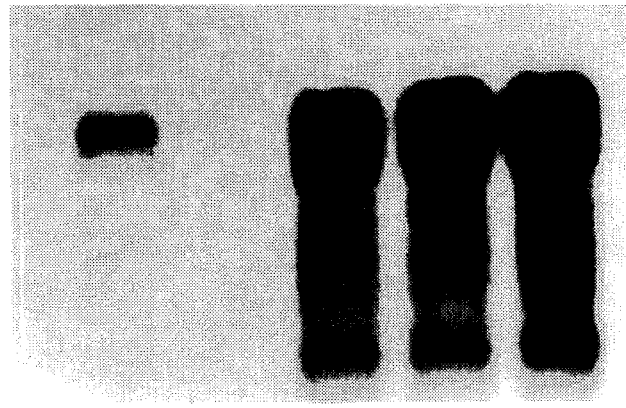

FIGS. 7A–D are Northern blots showing mitochondrial partitioning of transcripts derived from pMRP-F. FIG. 7a shows transcripts of pMRP-F detected by probe 1; FIG. 7b is endogenous MRP-RNA detected by probe 3; FIG. 7c is U1 RNA (nuclear marker); 7d is 16S mitochondrial ribosomal RNA (mitochondrial marker): Lane 1, total cellular RNA; lane 2, in vitro transcript of pMRP-F; lanes 3, 4 and 5, mitochondrial RNAs isolated after 1st, 2nd and 3rd fractionation steps, respectively (see FIG. 2). Ten µg of total or mitochondrial RNA were loaded in each lane in panel a, 5 µg were loaded in panels b–c, and 2 µg were loaded in panel d.

Figure 8:
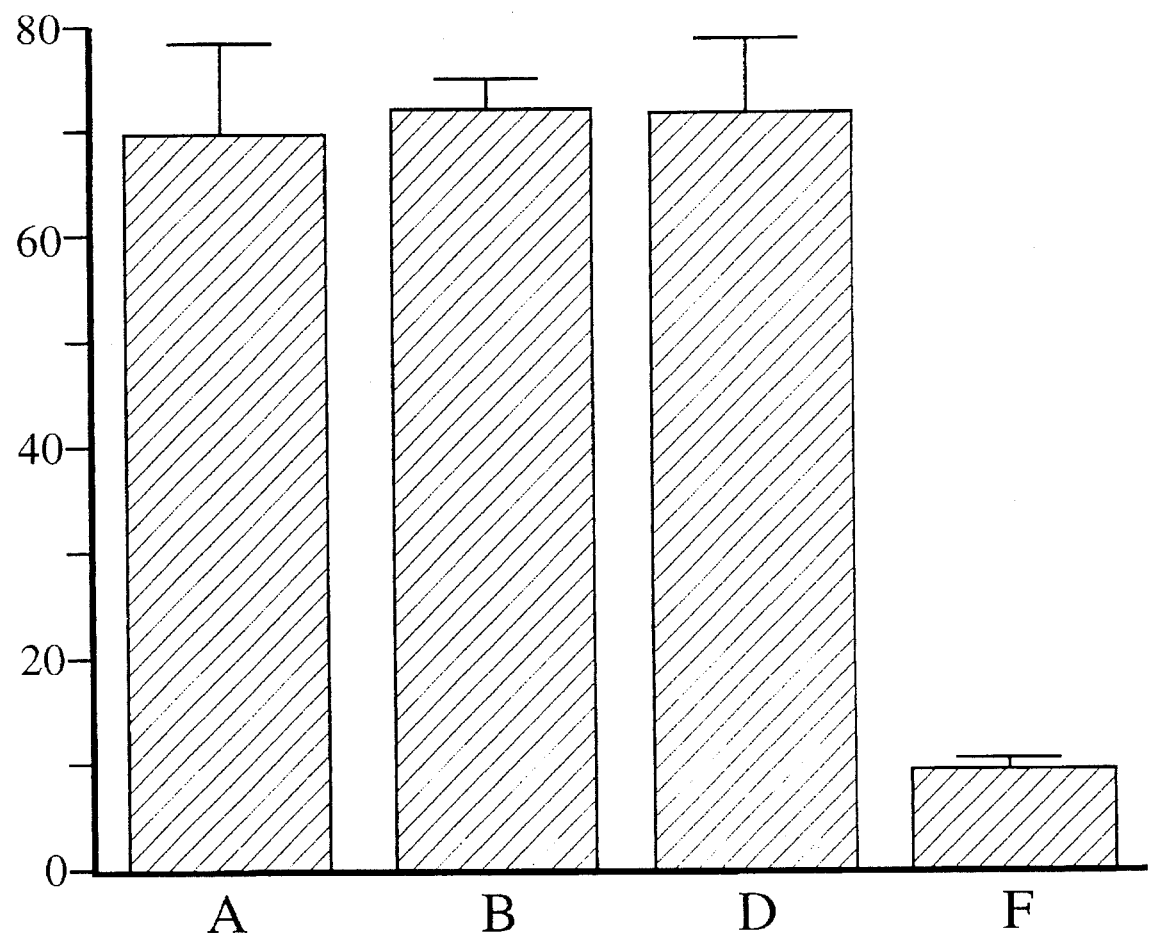

FIG. 8 shows mitochondrial partition ratios of mutant MRP-RNA transcripts. The relative mitochondrial partition ratios (see Methods) were calculated from the 3rd mtRNA preparation. Mean data from 2 independent transfection experiments are presented. A, B, D and F represent corresponding pMRP plasmids.

Figures 9A, 9B, 9C:
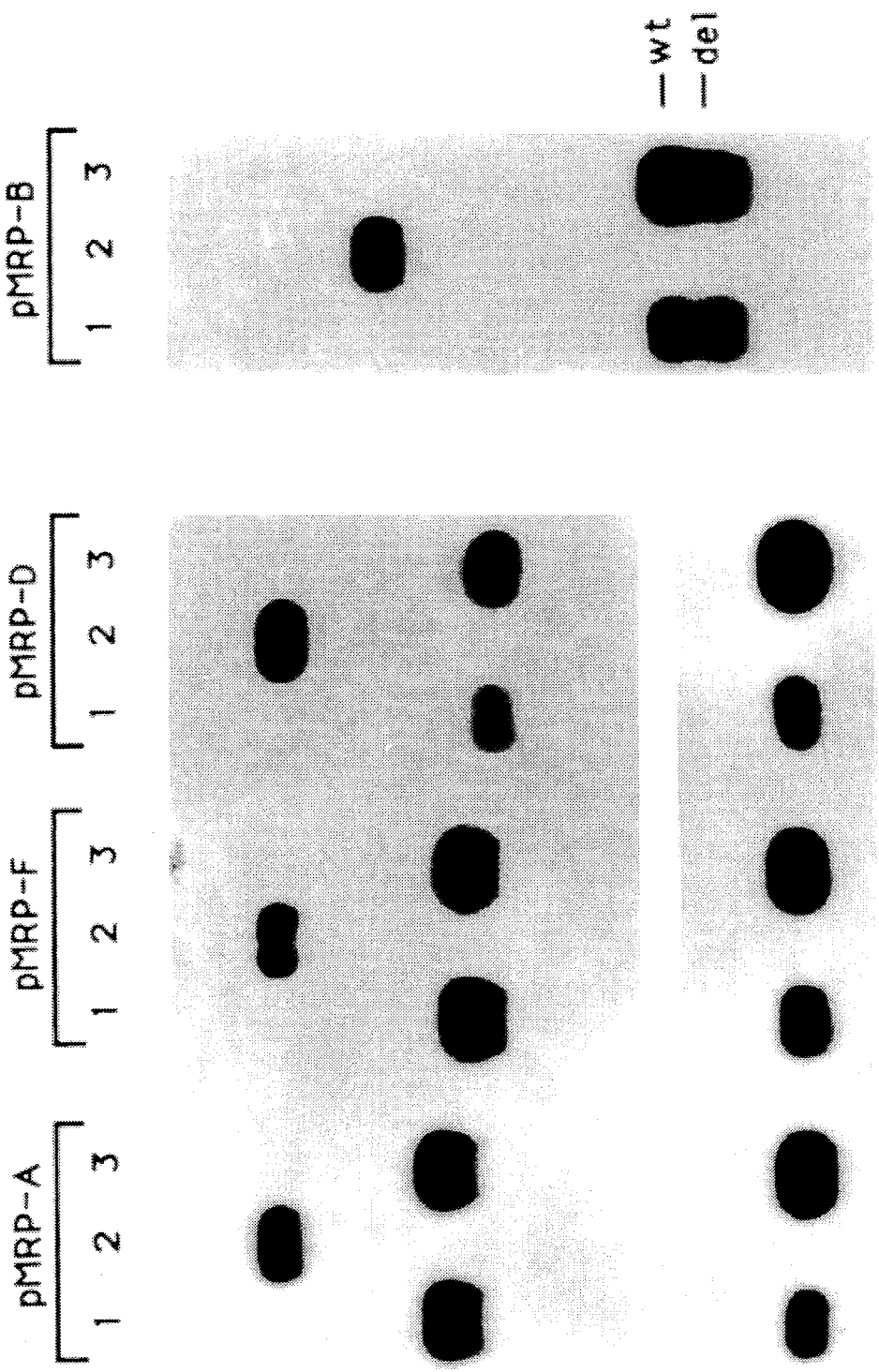

FIGS. 9A–C are Northern blot hybridizations showing nuclear partitioning of mutant MRP-RNAs. FIG. 9a: transcripts of pMRP-A, pMRP-F, and pMRP-D detected by probe 1. FIG. 9b: endogenous MRP-RNA detected by probe 3. FIG. 9c: transcripts of pMRP-B (del) and endogenous MRP-RNA (wt) detected by probe 2. Lane 1, total cellular RNA. Lane 2, in vitro transcripts of mutant MRP-RNAs. Lane 3, nuclear RNA. Three µg of nuclear or total cellular RNA were loaded in each lane.

Figure 10:
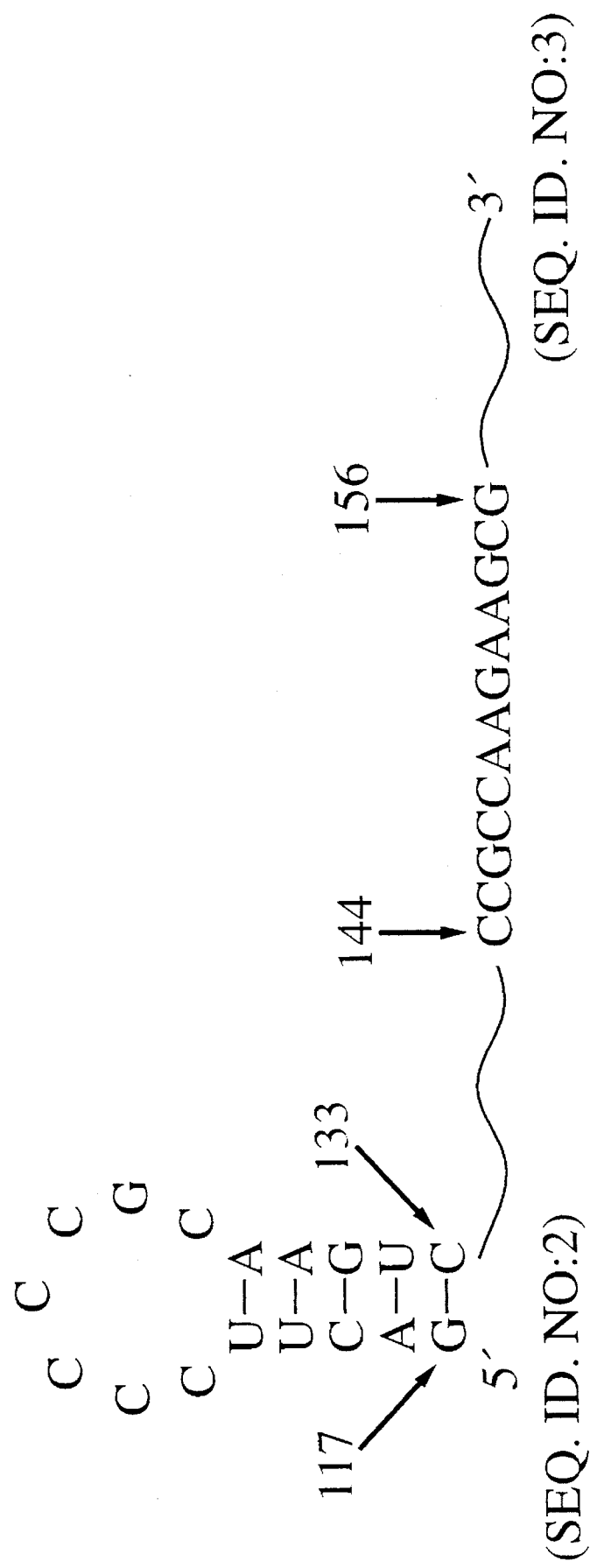

FIG. 10 shows the sequence and predicted secondary structure of the region of mouse MRP-RNA deleted in pMRP-F. The stem-loop and the region of sequence identity to the rat and human MRP-RNA genes are shown as SEQ ID NO: 2 and 3, respectively. The nucleotide positions correspond to those described by Topper and Clayton (1990b).

Figure 11:
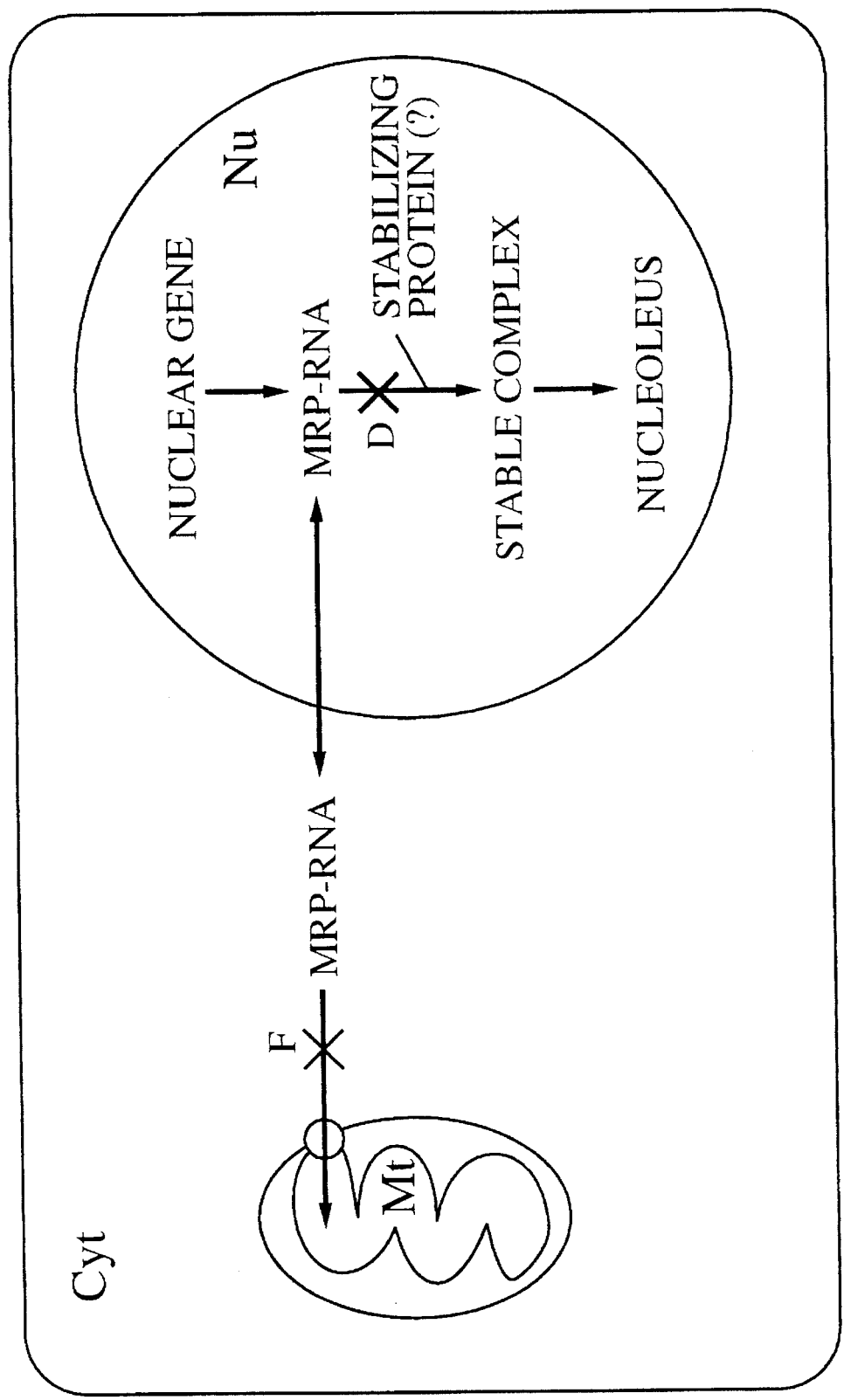

FIG. 11 is a summary illustration of intracellular trafficking of MRP-RNA. Nu: nucleus. Cyt: cytoplasm. Mt: mitochondrion. F: pMRP-F. D: pMRP-D.

Figure 12:
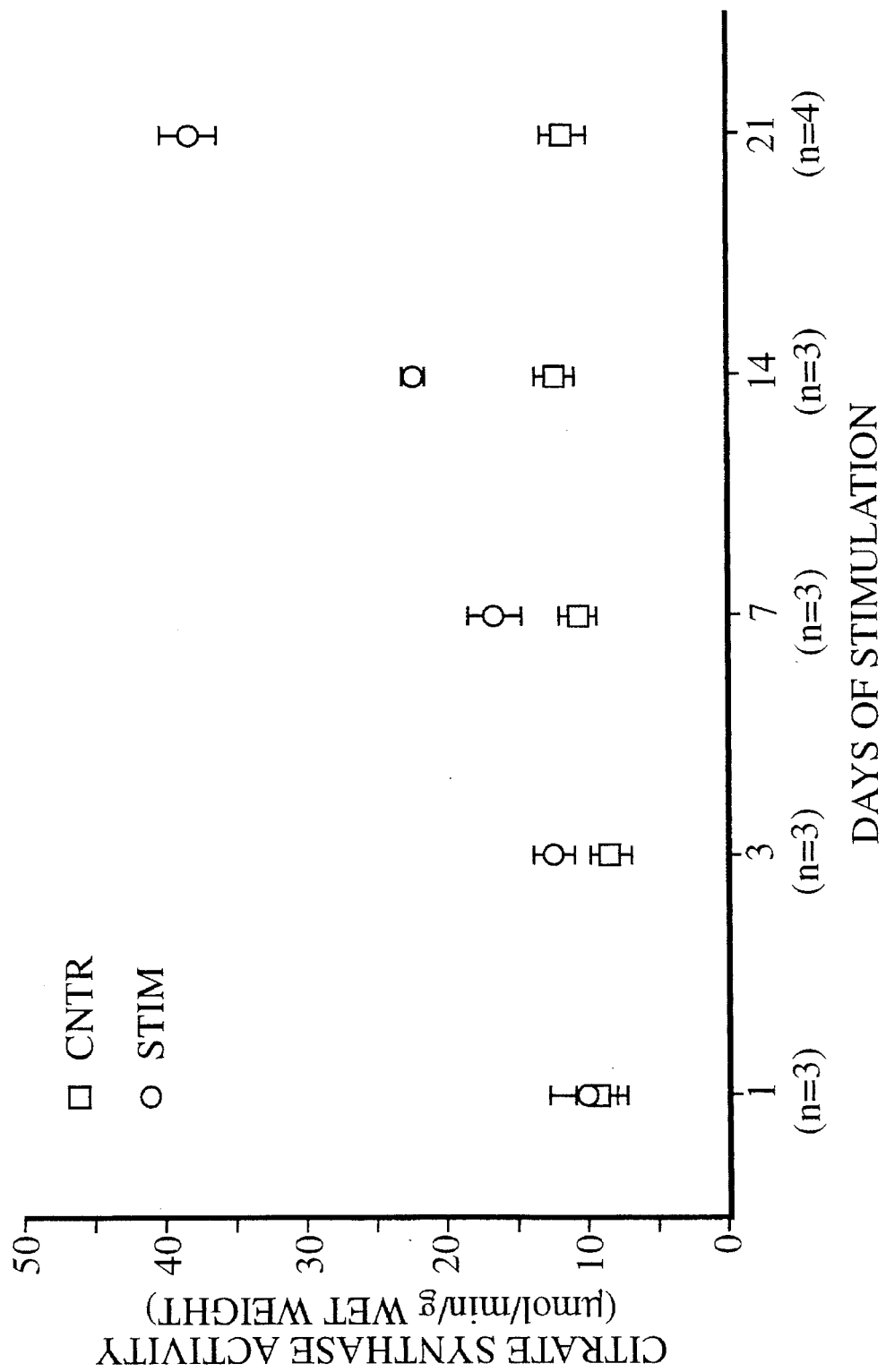

FIG. 12 shows the effects of motor nerve stimulation on specific activity of citrate synthase in skeletal muscle. Symbols depict mean values (±SE) from tibialis anterior muscles from adult rabbits that were stimulated (STIM: closed circles) for the indicated duration (1–21 days) and compared to contralateral, unstimulated control (CNTR: open squares) muscles from the same animals.

Figure 13B:
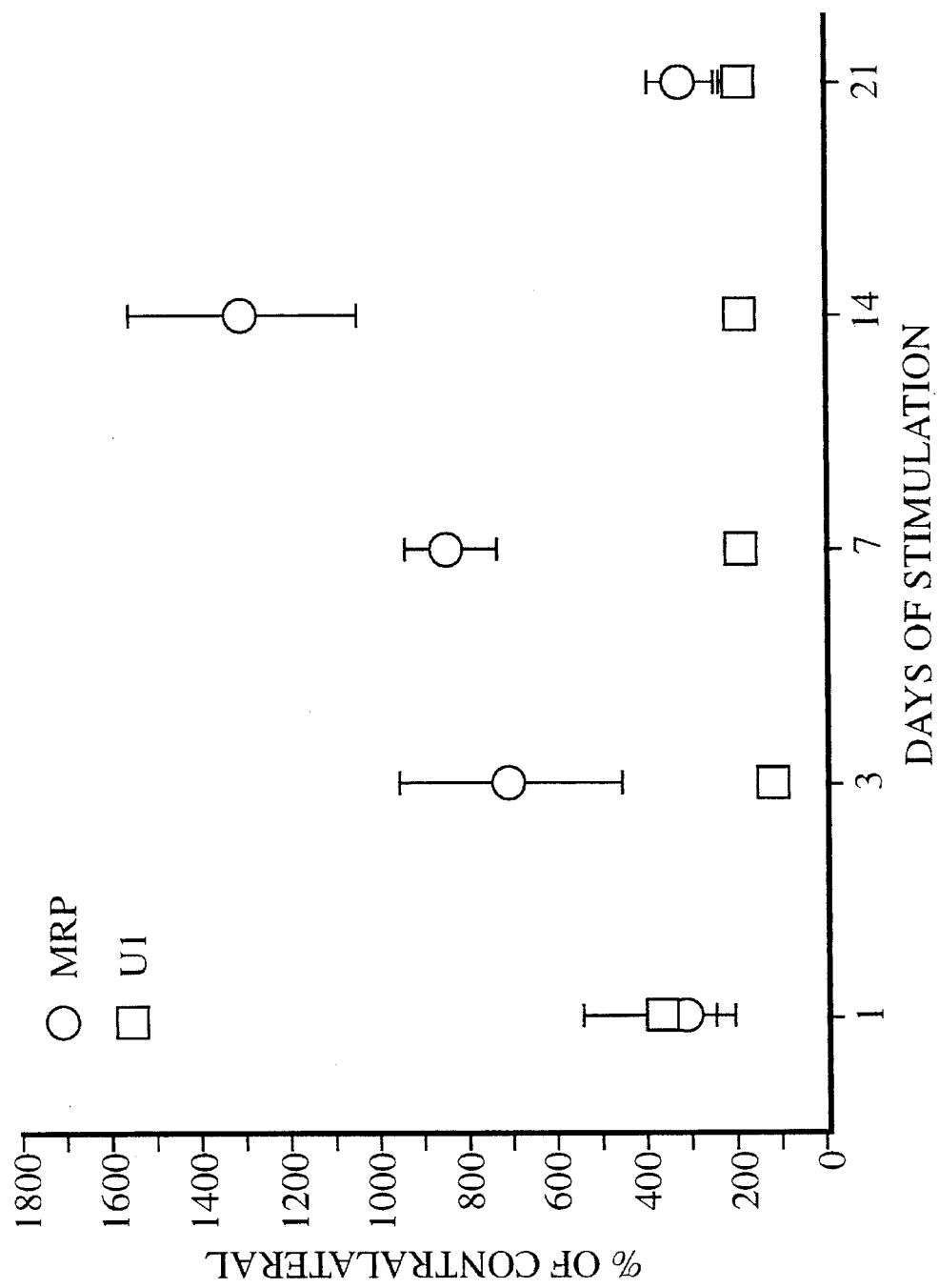

FIGS. 13A–B show effects of motor nerve stimulation on expression of MRP-RNA and U1 snRNA in skeletal muscle; FIG. 13A shows representative Northern analysis using antisense MRP-RNA as probe. Each lane was loaded with 5 µg of total RNA from unstimulated control or stimulated muscles of the same rabbit. The duration of stimulation (1–21 days) is indicated; FIG. 13B shows summary data. Densitometric estimates of MRP-RNA and U1 snRNA abundance in stimulated muscles at each time point are presented as a percentage of the abundance in contralateral, unstimulated muscles from the same animal (n=3 animals at each time point). Closed circles depict the expression of MRP-RNA and open squares depict expression of U1 snRNA (mean±SE).

Figure 14:
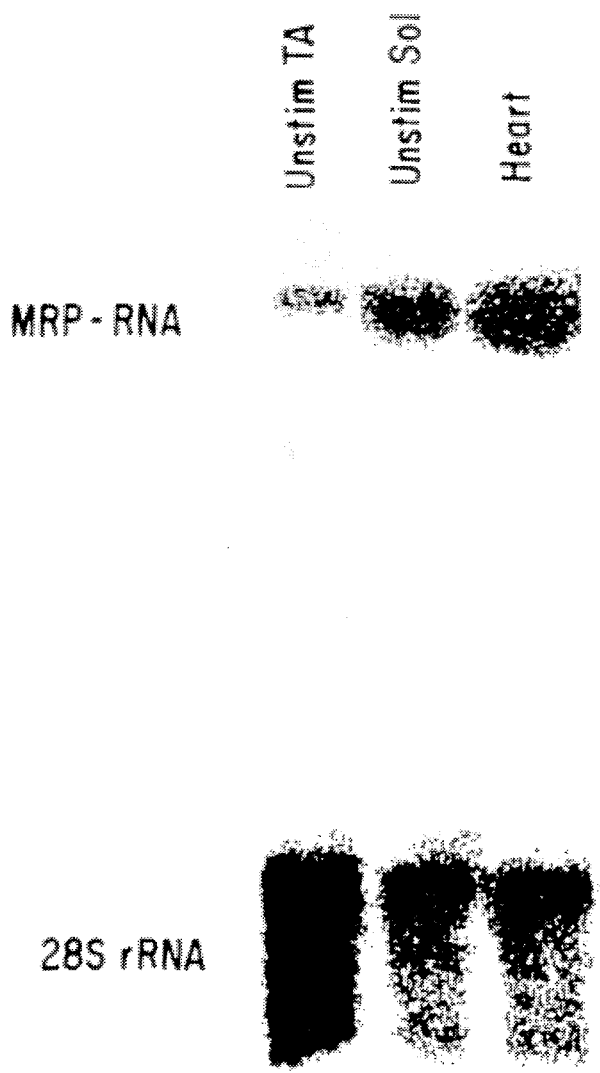

FIG. 14 shows expression of MRP-RNA in specialized subtypes of rabbit striated muscles. Northern blot probed with antisense MRP-RNA. Each lane was loaded with 5 µg of total RNA from mitochondria-poor tibialis anterior (TA) skeletal muscle or mitochondria-rich soleus (Sol) or cardiac (Heart) muscles from the same rabbit.

Figure 15A:
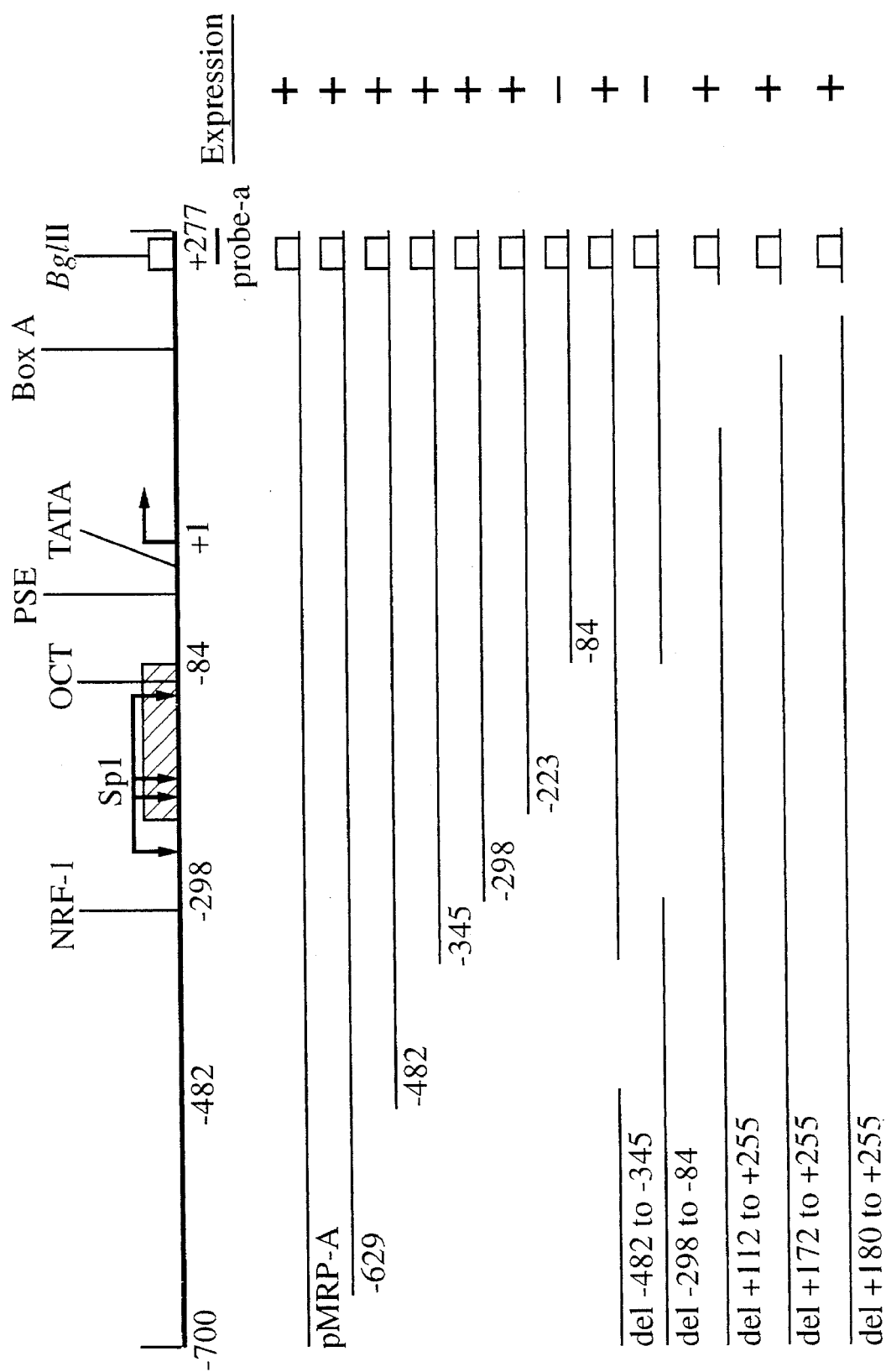
Figure 15B:
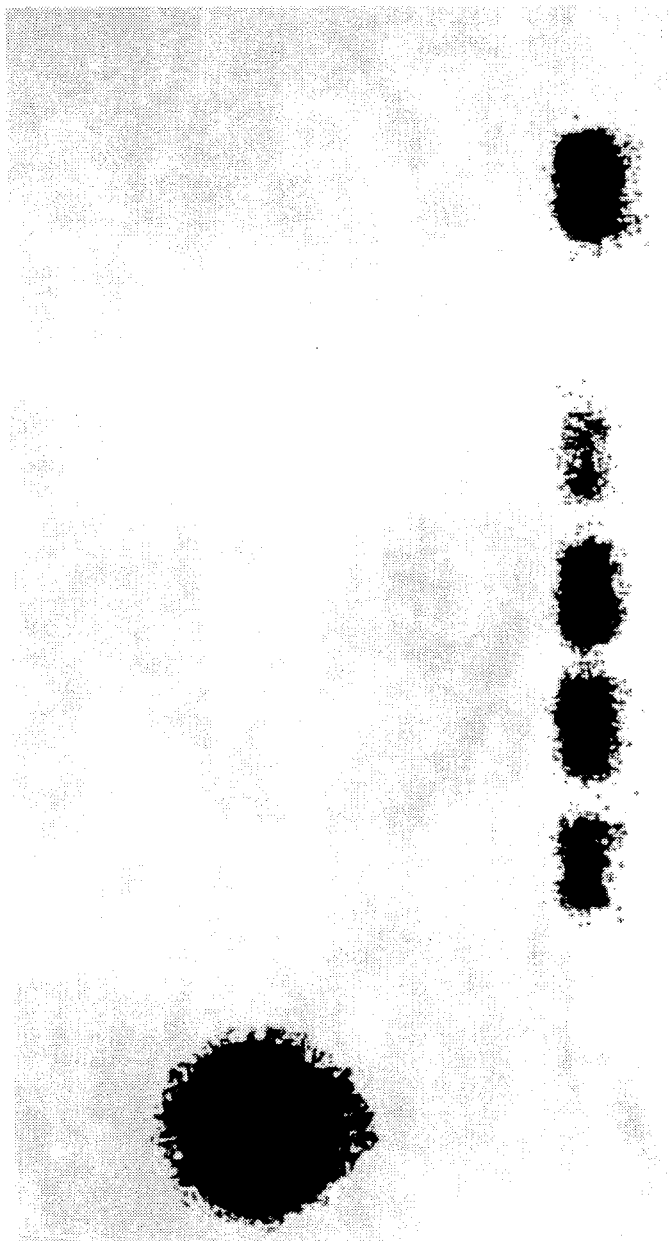
Figure 15C:
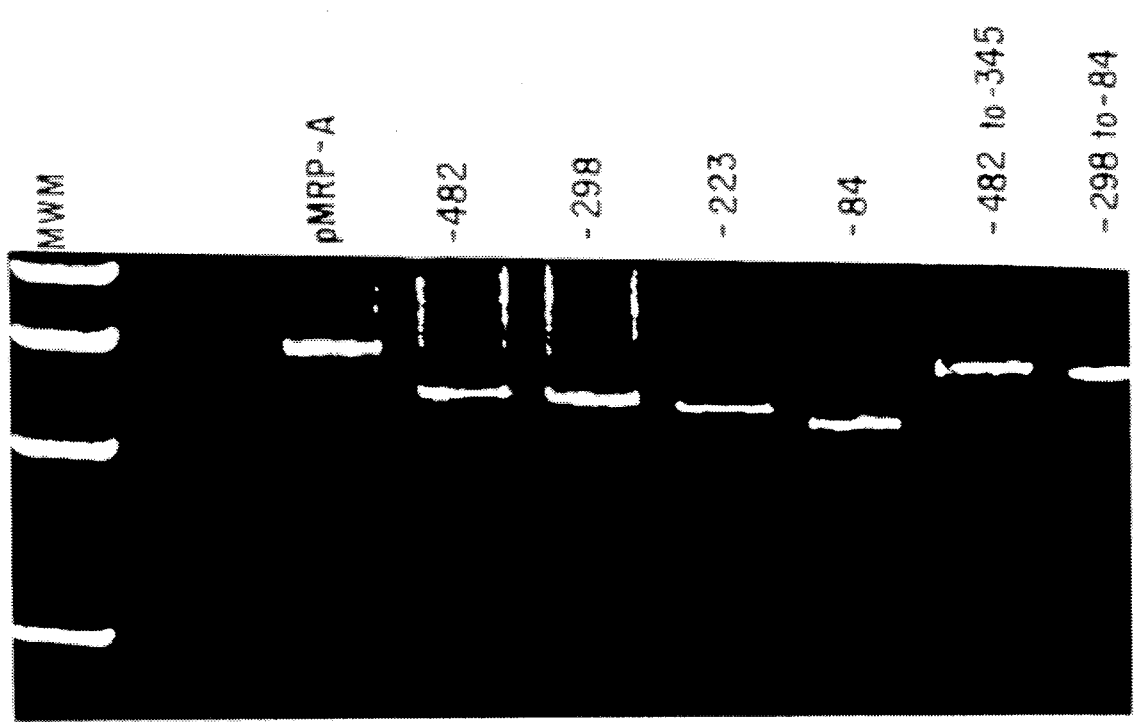

FIGS. 15A–C indicates the transcriptional control of the mouse MRP-RNA gene: FIG. 15A: Diagram of deletion strategy and summary of results. A schematic diagram of the mouse MRP-RNA gene indicates the transcriptional start site (arrow), the transcriptional termination site (+277), and the location of sequences similar to transcriptional control elements (NRF-1, Sp1, OCT, PSE, TATA, Box A) previously characterized in other genes (see text). A Bgl II linker (open square) was engineered into the transcribed portion of the gene so that transgene products could be distinguished from endogenous MRP-RNA by hybridization to an oligonucleotide probe (probe-a) under conditions of high stringency. The pMRP-A construct served as the parent for construction of deleted forms of the mouse MRP-RNA gene. These are identified either by the 5' terminus of MRP-RNA upstream sequences included in the construct, or by the 5' and 3' boundaries of internal deletions, relative to the transcriptional start site. An upstream region essential for expression in C2C12 myogenic cells is indicated (shaded rectangle); FIG. 15B: Representative Northern analysis of MRP-RNA transgene expression in C2C12 myogenic cells. Each lane was loaded with 5 µg of total RNA from cells transfected with the indicated constructs (see FIG. 15A). As indicated by the absence of a hybridization signal in mock transfected cells, the antisense oligonucleotide probe did not detect endogenous MRP-RNA under the stringency conditions used in this assay; FIG. 15C: Hirt analysis, in which ethidium bromide staining indicates approximately equal abundance of the transfected plasmids following introduction of different MRP-RNA constructs. These are identified as described in 15A (MWM= molecular weight markers).

Figure 16A:
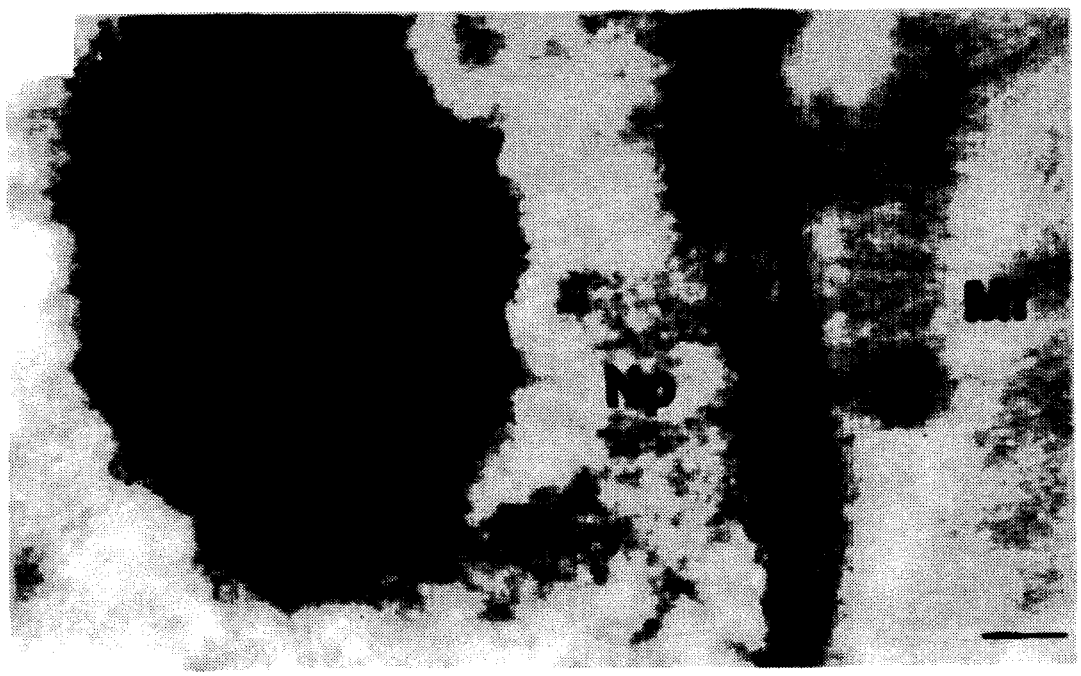
Figure 16B:
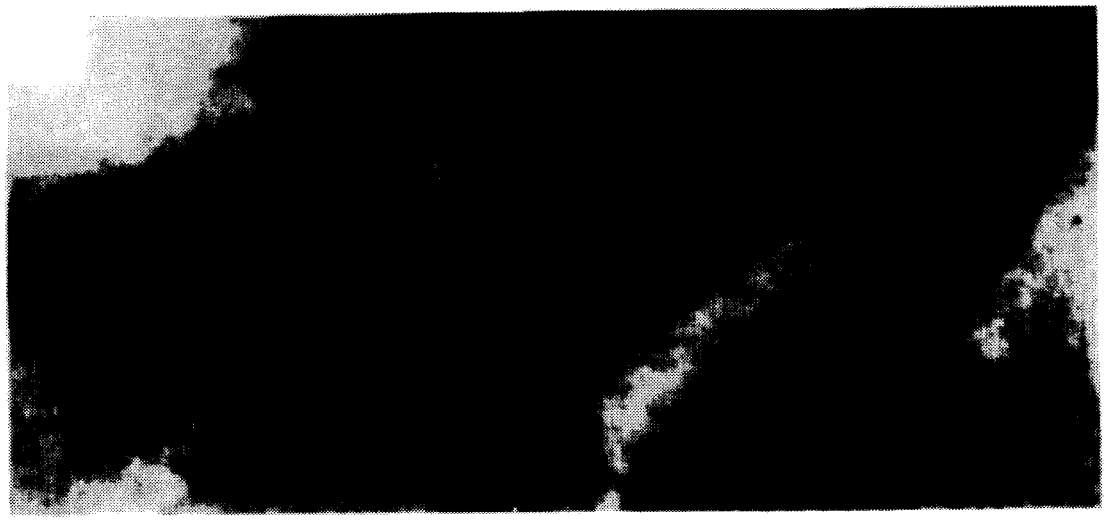

FIGS. 16A–B depicts intracellular localization of MRP-RNA by electron microscopy. In situ hybridization of a biotinylated RNA probe complementary to MRP-RNA within a cardiomyocyte. Probe was detected by immunogold-labeling (10 nm gold particles). Intracellular compartments shown include nucleoplasm (Np), nucleoli (No), myofibrils (Mf), and mitochondria (Mt). FIG. 16A; nucleolar binding of the antisense MRP-RNA probe, primarily within the granular sub-compartment. Magnification is 25,000×; bar= 200 nm. FIG. 16B; mitochondrial binding of the antisense MRP-RNA probe. Magnification is 40,000×; bar= 200 nm.

Figure 17:
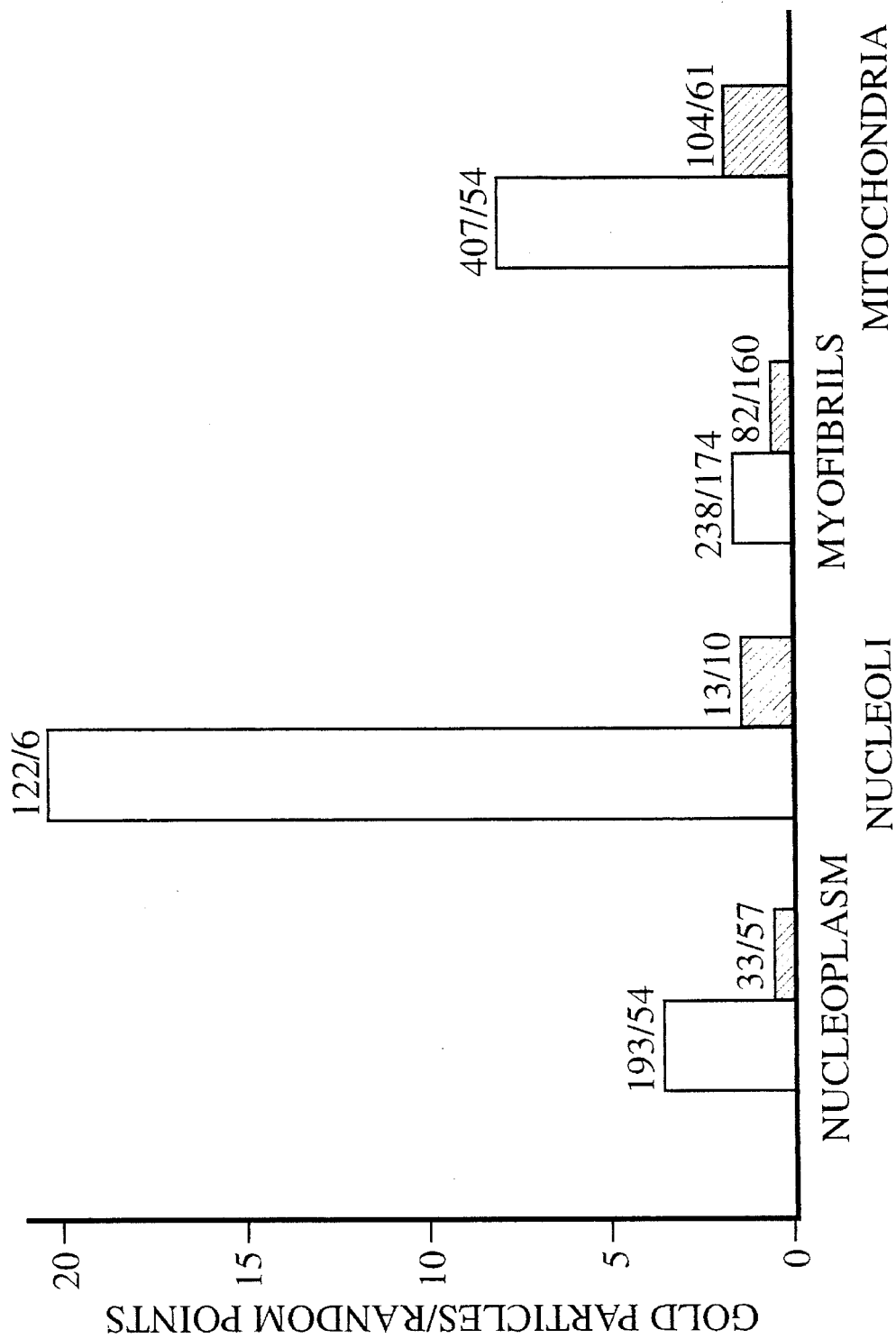

FIG. 17 depicts a quantitative analysis of the intracellular location of MRP-RNA. A systematic random sampling technique (Gundersen and Jensen, 1987) was applied to determine the relative abundance of MRP-RNA within each of four intracellular compartments (nucleoplasm, nucleoli, myofibrils, and mitochondria) after hybridization to either the antisense MRP-RNA probe (solid bars) or the control probe (hatched bars). Myofibrils occupy virtually all of the extramitochondrial cytoplasmic space in cardiomyocytes. The vertical axis depicts the ratio of gold particles versus random points, and provides a measure of bound probe relative to the area occupied by each of the four intracellular compartments within the sections. The control probe provides an estimate of non-specific binding. Actual counts are shown above each bar. Data were obtained by analysis of 24 randomly selected, scored by an experienced observer blinded to the identity of the probes. Similar results were obtained in each of three separate quantitative analyses of independent hybridization reactions.

DETAILED DESCRIPTION OF PREFERRED EMBODIMENTS

The present invention relates to the discovery of specific sequence elements that direct RNA to the mitochondria. By employing systematic mutations scanning through 90% of the coding region of the mouse MRP-RNA gene, a 58 nt region was identified. This RNA was found to be essential for import of the transcript into mitochondria. The same region, however, was not required for transcription, nuclear partitioning, or stability of the transcript in the cytoplasmic compartment. Certain other mutations within the MRP-RNA coding region did not affect import properties, indicating that specific sequence elements are required to direct RNA to a mitochondrial import pathway.

The disclosed results indicate that transcriptional control elements sufficient to direct efficient transcription of the gene reside within the proximal 700 bp of 5' flanking DNA. This upstream region of the mouse MRP-RNA gene includes an array of regulatory motifs similar to those of the U6 and 7SK RNA genes (Chang and Clayton, 1989; Yuan et al., 1989; Topper and Clayton, 1990b). Deletions of either the putative distal or proximal sequence elements from the MRP-RNA promoter eliminate transcription. These results place the MRP-RNA gene with U6 and 7SK RNA as members of the set of RNA polymerase (Pol III)-transcribed genes that are controlled by upstream sequences without a requirement for internal elements governing transcription (Murphy et al., 1987; Carbon et al., 1987; Das et al., 1988; Kunkel and Peterson, 1988; Waldschmidt et al., 1991).

One of the mutants (pMRP-D) described herein produced transcripts that appeared to exhibit reduced stability. Notably, these transcripts lacked the region of MRP-RNA previously identified as containing the binding site for To/Th antigen, a nucleolar protein (Reimer et al., 1988) recognized by antisera from human patients with progressive systemic sclerosis and related autoimmune diseases (Yuan et al., 1991). Several lines of evidence indicated that binding of MRP-RNA to To/Th antigen may stabilize the RNA within the nucleus. The To/Th antigen has high affinity for MRP-RNA (Yuan et al., 1991), though the interaction is not completely selective among small nuclear RNAs. Immunoprecipitation with anti-To/Th antibody brings down both MRP-RNA and RNase P1-RNA (Gold et al., 1989; Yuan et al., 1991). Stabilization of small RNAs by protein binding has been documented previously in the interaction of 4S RNA with TFIIIA (Picard and Wegnez, 1979). The deletion in MRP-D appears to limit stabilization of the transcript within the nucleus by impairing binding to To/Th antigen. Targeting signals that direct nuclear stabilization and mitochondrial partitioning of MRP-RNA appear to reside in distinct and separable domains of the transcript. At least 10 nuclear peptides are found to be associated with nuclear MRP-RNA in immunoprecipitation assays using anti-To sera (Karwan et al., 1991), suggesting that the repertoire of proteins binding to MRP-RNA may be large.

The inventors have found that expression of the RNA subunit of RNase MRP (MRP-RNA) is subject to regulation by physiological stimuli that alter mitochondrial biogenesis. Both the rapidity (<1 day) and magnitude (>10-fold) of the induction of MRP-RNA within skeletal muscle subjected to motor nerve stimulation are notable in comparison to pretranslational responses of other genes that are regulated by this stimulus (Williams et al., 1986; Annex et al., 1991; Williams et al., 1987; Hood et al., 1989). Expression of transcripts of several nuclear genes encoding mitochondrial proteins, including citrate synthase and subunits of cytochrome oxidase and $F_1F_0$ATPase are induced by nerve stimulation, but the onset of these responses is not apparent until 3–10 days after the onset of nerve stimulation. Maximal induction of these nuclear genes requires 21 days and does not exceed 5-fold. Among non-mitochondrial proteins, mRNA species encoding myoglobin and slow isoforms of contractile proteins are increased in abundance by 10-fold or greater, but these responses also require 3–10 days to emerge, and are not complete until 21 days.

With respect to mitochondrial DNA (mtDNA) and expression of mitochondrial genes, the time course of the response of MRP-RNA in skeletal muscles subjected to continuous motor nerve stimulation is consistent with a role for MRP-RNA in modulating the rate of mtDNA replication. Previously, independent sets of experiments showed that copy number of mtDNA is increased by this stimulus. This response becomes measurable (>2-fold after 3–10 days, increases markedly by 3–10-fold after 14–21 days, Williams et al., 1986; Williams, R. S., 1986; Annex et al., 1991), but declines thereafter to equilibrate at levels 1.5- to 2-fold above control values. Expression of rRNA and mRNA products of mitochondrial genes tracks almost identically with these adaptive responses of mtDNA, suggesting that variations in expression of mitochondrial genes in striated muscle are determined predominately by gene dosage in these cells, rather than by modulation of transcriptional efficiency (Williams et al., 1986; Williams, R. S., 1986). Stimulation-induced changes in abundance of MRP-RNA occur in parallel to, but temporally in advance of, increases in mtDNA, a time course predicted for a regulatory factor.

A regulatory role for RNase MRP in controlling mtDNA replication is suggested by its putative function in cleaving nascent transcripts from the light strand promoter to generate short RNA primers for DNA synthesis originating from the heavy strand origin of replication (Chang and Clayton, 1987; Clayton, D. A., 1991). Thus, the activity of RNase MRP serves functionally to shift the mitochondrial genome from a transcriptional mode into a replicative mode.

The presence of a relatively abundant cytoplasmic pool of MRP-RNA within mitochondria-rich skeletal and cardiac myocytes has been shown using in situ hybridization. Similarly, when myocytes rather than HeLa cells are examined, levels of MRP-RNA present in purified mitochondria exceed levels of U1 snRNA by at least an order of magnitude.

Induction of MRP-RNA may contribute to the increase in rRNA and in translation of certain genes (Annex et al., 1991) that occur in the early phase (days 1–3) of the adaptive response of skeletal muscle to continuous nerve stimulation. The rise in U1 snRNA that accompanies the induction of MRP-RNA expression within this early period may indicate a general activation of genes encoding small RNAs involved in RNA processing during this early period. The disproportionate changes in MRP-RNA and U1 snRNA during the period of most rapid mitochondrial biogenesis (days 7–14) indicate, however, that these two genes are subject to selective regulation as well.

The observation that MRP-RNA gene expression is induced more rapidly than other nuclear genes in response to nerve stimulation makes the MRP-RNA gene an attractive model for identification of transcriptional control pathways that link physiological activity of striated muscle to changes in gene expression.

Findings from in vivo expression assays of plasmid constructions transfected into C2C12 myogenic cells permit two major conclusions. First, it was demonstrated that sequences sufficient to direct transcription of the mouse MRP-RNA gene in this cell background are included within the proximate 5' flanking region of the gene, and that intragenic transcriptional control elements appear not to be required. This finding places MRP-RNA within the class of small RNA genes transcribed by Pol III that includes U6, but distinguishes MRP-RNA from tRNA and 5S RNA genes that require intragenic sequence elements. Second, the deletional analysis indicates that an upstream region from −223 bp to −84 bp (relative to the transcription start site) contains sequences required for transcription.

This upstream region of the MRP-RNA gene includes consensus binding sites for Sp1 and an octamer motif. Interestingly, the results indicate that an apparent binding site for nuclear respiratory factor 1 (NRF–1) located between −322 and −301 is not necessary for basal expression of MRP-RNA in these cultured cells. NRF–1 is implicated in transcriptional control of several nuclear genes encoding mitochondrial proteins (Evans and Scarpulla, 1989). This sequence motif and its cognate binding factor may be dispensable for basal expression of MRP-RNA in resting cells, but nevertheless may be involved in the induced expression of MRP-RNA that results from physiological stimuli such as nerve stimulation.

Expression of MRP-RNA in specialized subtypes of rabbit striated muscles varies in proportion to respiratory activity. In addition, expression of MRP-RNA was induced in skeletal muscle by chronic stimulation of the motor nerve, a potent stimulus to mitochondrial biogenesis. It was also determined that the proximate 5' flanking region of the mouse MRP-RNA gene is sufficient to direct transcription in a muscle cell background. These results are consistent with a regulatory role for MRP-RNA and for RNase MRP in modulating mtDNA replication, and in maintaining the stoichiometry of subunits of mitochondrial enzymes that are derived from nuclear and mitochondrial genes.

EXAMPLE 1

A number of small RNA genes transcribed by RNA polymerase III (Pol III) require internal regulatory elements for efficient transcription (Bogenhagen et al., 1980; Sakonju et al., 1980; Galli et al., 1981; Hofstetter et al., 1981; Ullu and Weiner, 1985). In vitro transcription assays indicated that MRP-RNA also was transcribed by Pol III (Yuan and Reddy, 1991). With this information, internal deletions were made to determine if transcription was abolished. This was accomplished by constructing mutant plasmids designed to express mutant transcripts after transfection into mammalian cells. This resulted in the identification of a transcript that identified a specific mitochondrial transport RNA.

Construction of Mutant MRP-RNA Genes

Figure 1:
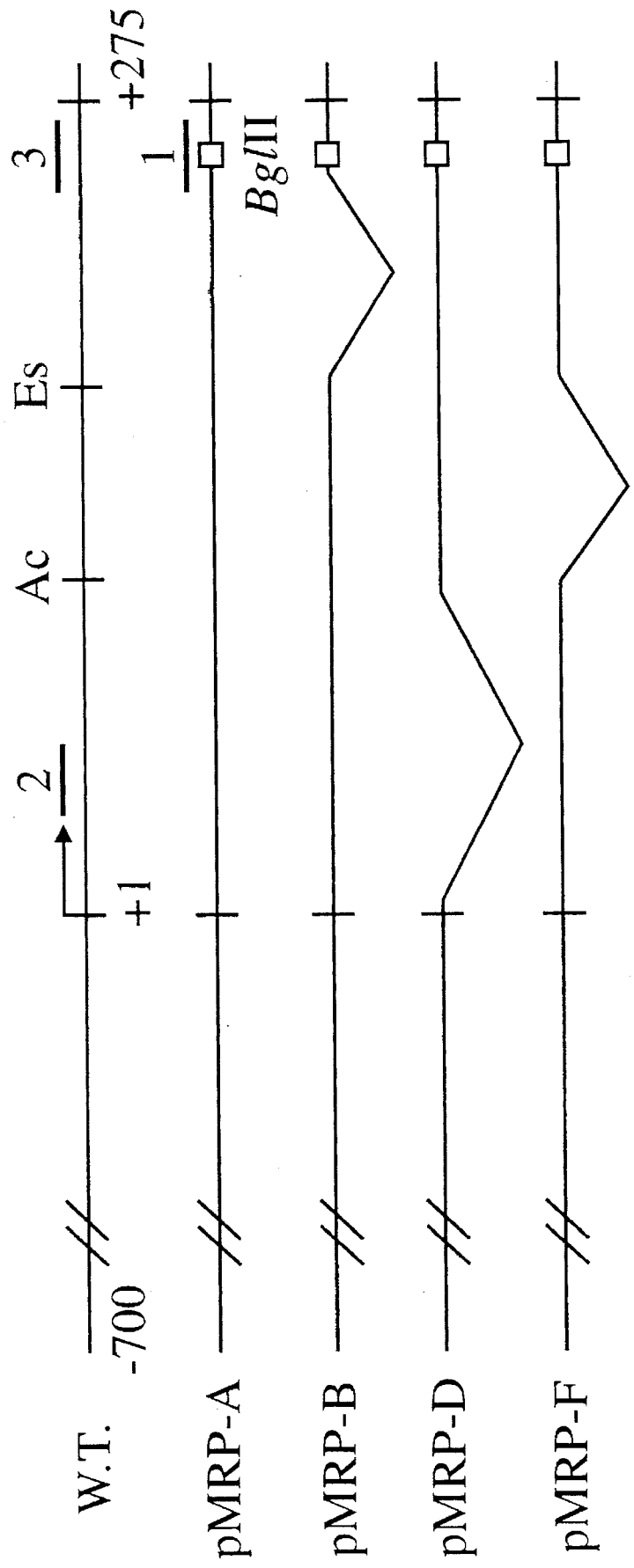
FIG. 1 is a schematic representation of mutant MRP-RNA constructs. Numbers beneath wild type gene (W.T.) reflect the 5' flanking sequences included in the plasmid constructs (−700), the start site for transcription (+1 and arrow), and the termination site (+275), respectively. The positions complementary to the three oligonucleotide probes are shown by corresponding numbers and bars. The box represents the engineered Bgl II site, and deletions are indicated by gaps. Ac: Acc I. Es: Esp. I.

The MRP-RNA gene was cloned by PCR amplification from mouse genomic DNA using primers based on the published sequence (Topper and Clayton, 1990b). The MRP-RNA gene clone, pMRP-A, consists of 273 bp of coding region, 700 bp of 5' flanking DNA and the 3' transcriptional termination sequence. A unique Bgl II site was engineered near to the 3' terminus of the coding region using Bgl II linker PCR primers (FIG. 1, pMRP-A). Deletion mutants were generated by PCR primer-guided synthesis and Acc I and Esp I restriction to remove the selected segments of the MRP-RNA coding region (FIG. 1). All the constructs were cloned into pBluescript KS (Strategéne, La Jolla, Calif.) and verified by restriction mapping and sequencing.

Cell Culture and Transfection

Mouse C2C12 myoblast cells were grown in Dulbecco's modified Eagle's medium with 10% fetal calf serum, 5% chick embryo extract and 20 units/ml penicillin-streptomycin. Calcium phosphate transfections were performed as described previously (Li et al., 1990). Thirty micrograms of plasmid DNA were added to each 100-mm dish. For transcriptional analysis, the duplicate plates of transfected cells were mixed. One half was used to extract transfected plasmid (Hirt, 1967) as a control for the efficiency of transfection, and the other half was employed for RNA isolation and Northern blot hybridization.

In Vitro Transcription

Nuclear and cytosolic extracts were prepared from Hela cells as described previously (Dignam et al., 1983). The in vitro transcription reactions were performed in 30 μl of reaction volume containing 600 ng plasmid DNA and 7.5 μl each of nuclear and cytosolic extract using a modified procedure (Ullu and Weiner, 1984). The reaction products were resolved by electrophoresis in 6% urea-potyacrylamide gels.

Isolation of Mitochondria and Nuclei

Figure 2:
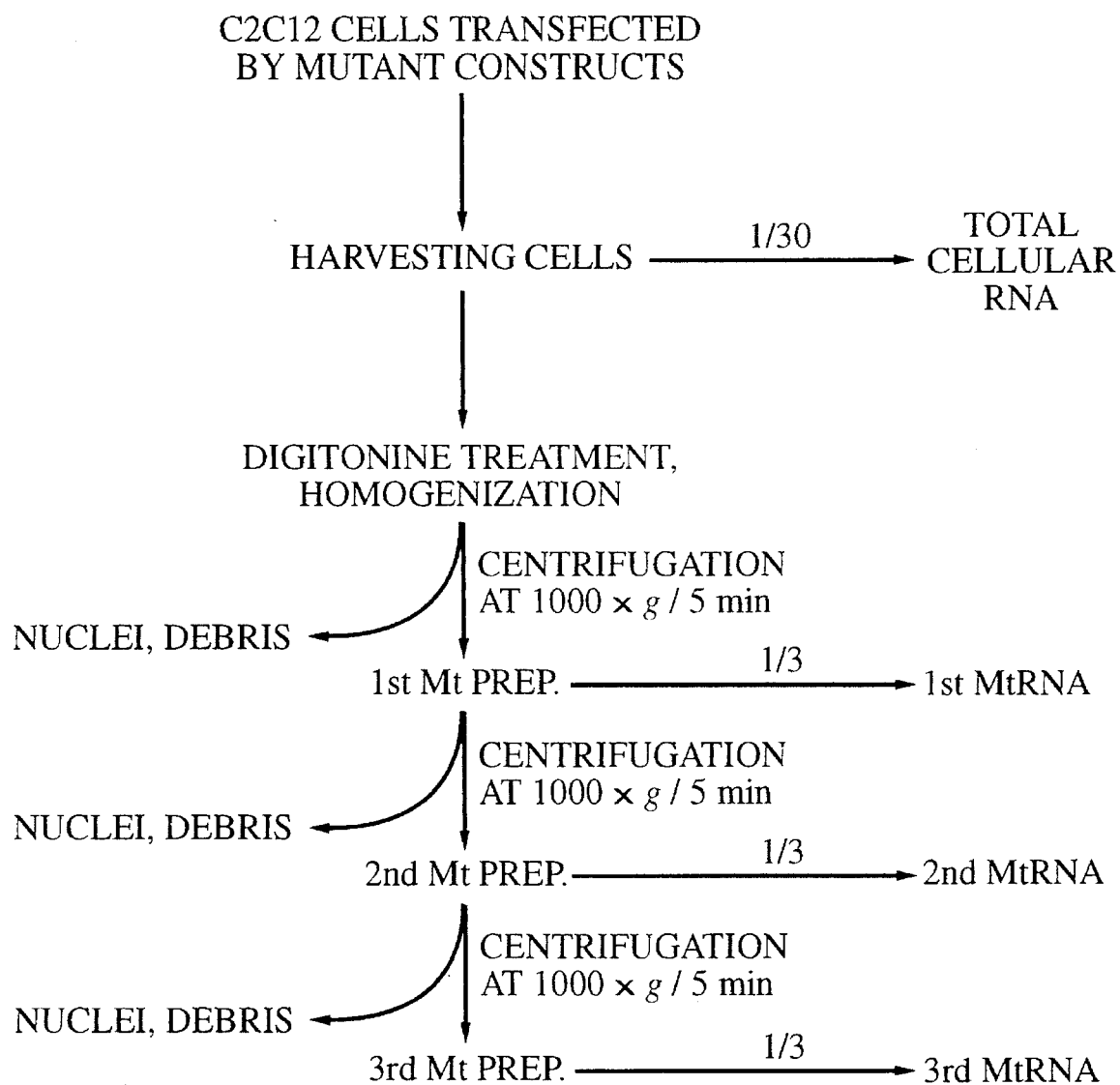
FIG. 2 is a protocol for fractionation of C2C12 cells.

Cellular fractions enriched in mitochondria were isolated as shown in FIG. 2. For each experiment, 20 plates of C2C12 cells were transfected with a mutant plasmid. One thirtieth of harvested cells were lysed directly to isolate total cellular RNA. The remaining cells were presolubilized with digitonin to facilitate isolation of mitochondria (Moreadith and Fiskum, 1984; Howell et al., 1986). Briefly, the cells were suspended in 4 volumes of mitochondria homogenization buffer (MtHB: 210 mM mannitol, 70 mM sucrose, 5 mM HEPES pH 7.3, 0.5% BSA) after three washes. Digitonin (5%) was added to a final concentration of about 0.5 mg/ml. The cells were washed once, resuspended in 4 volumes of MTHB and homogenized with a Dounce homogenizer (6–15 strokes). The lysate was diluted with 0.5× MTHB and centrifuged at 8,000 g for 10 minutes. After resuspending the pelleted mitochondria, nuclei and cell debris in 15 volumes of MTHB, the lysate was subjected to three consecutive centrifugations at 1000–1080 x g for 5 min each (2100–2200 rpm, Sorvall RT6000B centrifuge, H1000B rotor). An aliquot was removed from the supernatant of each low speed centrifugation step and centrifuged at 8000 x g for 10 min to produce increasingly purified mitochondrial fractions for RNA extraction (FIG. 2).

Nuclei were isolated in a parallel procedure. The nuclear pellets from the initial low speed centrifugation step were washed once with MTHB and once with 1 ml ionic buffer (10 mM HEPES pH 7.9, 150 mM KCl, 10 mM $MgCl_2$).

RNA Isolation and Northern Blot Hybridization

RNA was isolated by a modification of the guanidinium thiocyanate procedure (Sambrook et al., 1989). RNA samples were electrophoresed in 1.5% (for U1 and MRP-RNAs) and 1.1% (for ribosomal RNAs) denaturing agarose gels. The gel buffer contained 20 mM HEPES pH 7.5, 5 mM NaCl, 1 mM EDTA and 2.2M formaldehyde. After transfer to nylon membranes, Northern blot hybridizations were performed by standard techniques (Overhauser et al., 1987). Control MRP-RNA was synthesized in vitro from Hind III-linearized pMRP-A using T7 RNA polymerase, yielding a 1 kb RNA transcript.

Synthetic oligonucleotides were used as probes specific for detection of MRP-RNA, U1 RNA, 28S cytoplasmic ribosomal RNA, and 16S mitochondria ribosomal RNA. Three different oligonucleotide probes (see FIG. 1) were used to detect mutant and endogenous MRP-RNA transcripts:

MRP probe 1, 5'-GAATGAGatcTGTGGTTGGTGCG (mutant) SEQ ID NO: 4;
MRP probe 2, 5'-CATGTCCCTCGTATGTAGCCTAG (wild type) SEQ ID NO: 5;
MRP probe 3, 5'-GAGAATGAG<u>CCCCG</u>TGTGGTTG (wild type) SEQ ID NO: 6.

The 5 bases underlined in probe 3 were replaced in mutant constructs by the 3 bases underlined and indicated in lower case in probe 1.

RNA Quantitation and Data Analysis

Hybridization of $^{32}P$-labelled probes to specific bands in Northern blots was measured quantitatively using Imager-Quant or PhosphoImager (Molecular Dynamics, Sunnyvale, Calif.). Mitochondrial import of mutant MRP-RNA transcripts was calculated as follows:

$$\text{Mitochondrial Partition ratio} = \frac{\text{mito/total mutant MRP-RNA}}{\text{mito/total endogenous MRP-RNA}}$$

Nuclear partition ratios were calculated in a similar manner. Mutant MRP-RNA sequences were analyzed with the computer program SQUIGGLES (Zuker and Stiegler, 1981) to assess thermodynamic predictions of internal pairing and folding.

Plasmid Constructs for Expression of Mutant Transcripts

To identify sequences within the MRP-RNA required for mitochondrial targeting, plasmid constructions designed to express mutant transcripts after transfection into mammalian cells were prepared. A linker mutation plasmid, pMRP-A, was engineered with a 3 bp insertion and a 5 bp deletion at nt 251–255, yielding a 273 nt RNA transcript, two nucleotides shorter than wild type MRP-RNA. Three other plasmid constructions carried deletions designed to scan 90% of the coding region for putative import signals. The deletion in pMRP-B removed most of the 3' end of the gene from nt 181 to nt 255, while most of the 5' region (nt 6 to nt 115) was removed in pMRP-D, including the To/Th antigen binding domain (Yuan et al., 1991). The deletion in pMRP-F extended from nt 118 to nt 175 (SEQ ID NO: 9) and disrupted a sequence resembling an intragenic transcriptional control region (Box A) found within some small RNA genes transcribed by RNA polymerase III (Pol III) (Sakonju et al., 1980; Galli et al., 1981; Ullu and Weiner, 1985). All the mutant plasmids contained identical 5' promotor sequences and 3' flanking signals for transcriptional termination (FIG. 1).

Transcription of MRP-RNA Mutants

Figure 3A:
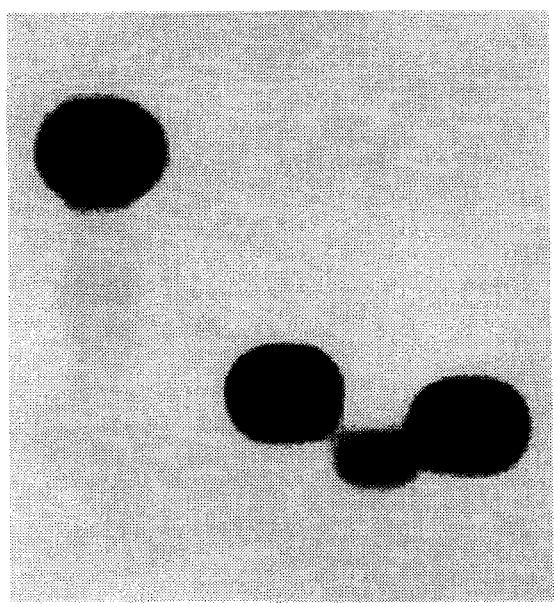
FIGS. 3A–C show expression of mutant MRP transcripts in the total pool of cellular RNA after transfection of C2C12 cells.
Figure 3B:
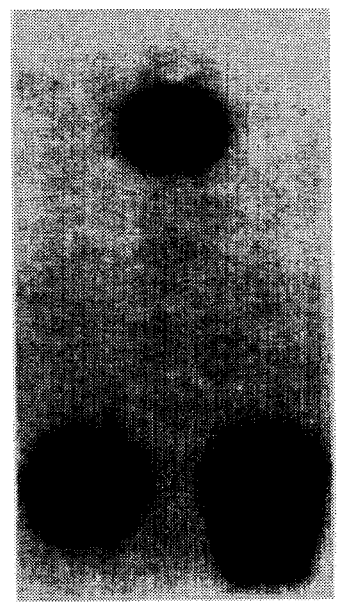

Mutant MRP-RNA plasmids were transfected into C2C12 myogenic cells and transient expression was detected by Northern blot hybridization with specific oligonucleotide probes. Probe 1 hybridized selectively to mutant MRP-RNAs transcribed from pMRP-A, pMRP-D and pMRP-F, but not to endogenous MRP-RNA (FIG. 3a). Probe 2 hybridized to both mutant and endogenous MRP-RNAs, but distinguished deleted forms by differences in size (FIG. 3b).

The results indicated that all of the mutant MRP-RNA constructs were transcribed. Plasmid pMRP-A, pMRP-F and pMRP-B produced transcript levels similar to each other (FIG. 3), and equivalent to the endogenous MRP-RNA band (FIG. 3b; FIG. 5a, lane 1; and FIG. 9c, lane 1). Disruption of the Box A-like element by the deletion in pMRP-F had no effect on the relative abundance of the resulting transcript relative to other constructs in which the box A-like element was undisturbed.

Figure 3C:
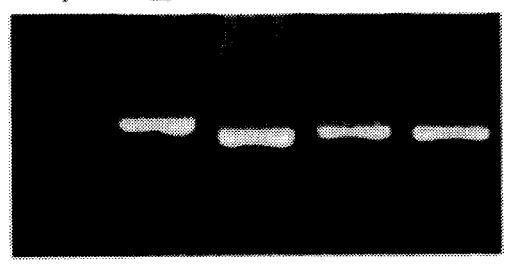

However, the deletion in pMRP-D resulted in reduced levels of transcript in the total cellular RNA pool (FIG. 3a). This difference was not attributable to reduced efficiency of transfection (FIG. 3c). In vitro transcription assays revealed that all of the mutant constructs were transcribed at an equivalent rate, suggesting that the reduced abundance of MRP-D transcripts resulted from more rapid degradation rather than from disruption of an internal control element important for transcription.

Assessment of Mitochondrial Partitioning

MRP-RNA was present mainly in the nucleus, and only a fraction of the total cellular pool was found in the mitochondrial compartment. For assessment of mitochondrial partitioning of MRP-RNA, mouse C2C12 myoblast cells were chosen because of their high mitochondrial content relative to other cell lines. The mitochondrial partitioning of heterologous MRP-RNA was examined through sequential mitochondrial preparations segregated from nuclei and cytosol. The final mitochondrial fraction was devoid of nuclear contamination as assessed by staining with Trypan Blue. A series of controls confirmed the authenticity of the mitochondrial fractions (FIG. 2) isolated from these cells. As shown in FIG. 4, U1 RNA (Carmo-Fonseca et al., 1991), chosen as a nuclear marker, thereby serving as a negative control for mitochondrial import, was abundant in the whole cell homogenate but was depleted during purification of mitochondria. Likewise, cytosolic (28S) ribosomal RNA was removed by the fractionation procedure. In contrast, 16S mitochondrial ribosomal RNA was markedly enriched in the mitochondrial fractions.

Mitochondrial Import of Foreign and Endogenous MRP-RNA

To examine mitochondrial import of foreign RNA sequences, the partitioning of MRP-A transcripts was compared with that of endogenous MRP-RNA. The small linker mutation within MRP-A permitted it to be distinguished readily from the endogenous gene product while introducing only minor alterations in the sequence of the transcript. Such minimal deviation from the endogenous sequence was considered unlikely to interfere with mitochondrial import of the pMRP-A transcript, thus permitting this construct to serve as a positive control for mitochondrial partitioning of products of other mutant MRP-RNA genes.

Figure 4A:
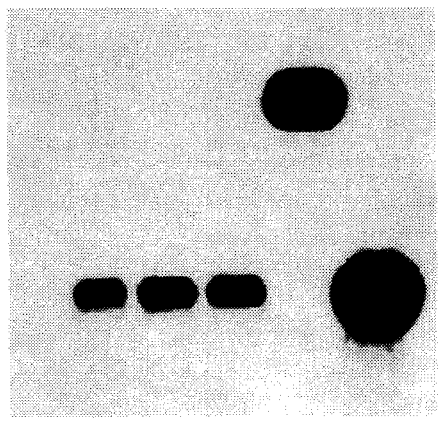
FIGS. 4A–F are Northern blots hybridization showing mitochondrial partitioning of transcripts derived from pMRP-A.
Figure 4B:
Figure 4C:
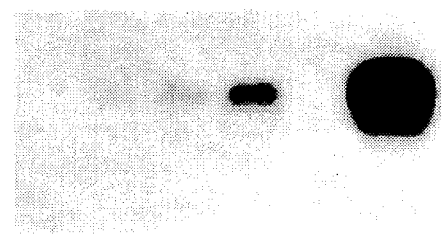
Figure 4D:
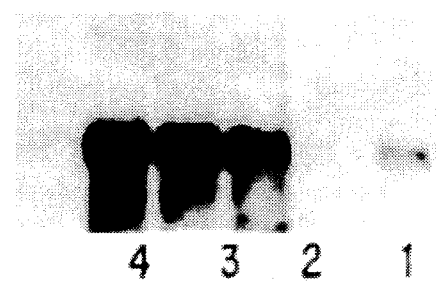
Figure 4E:
Figure 4F:
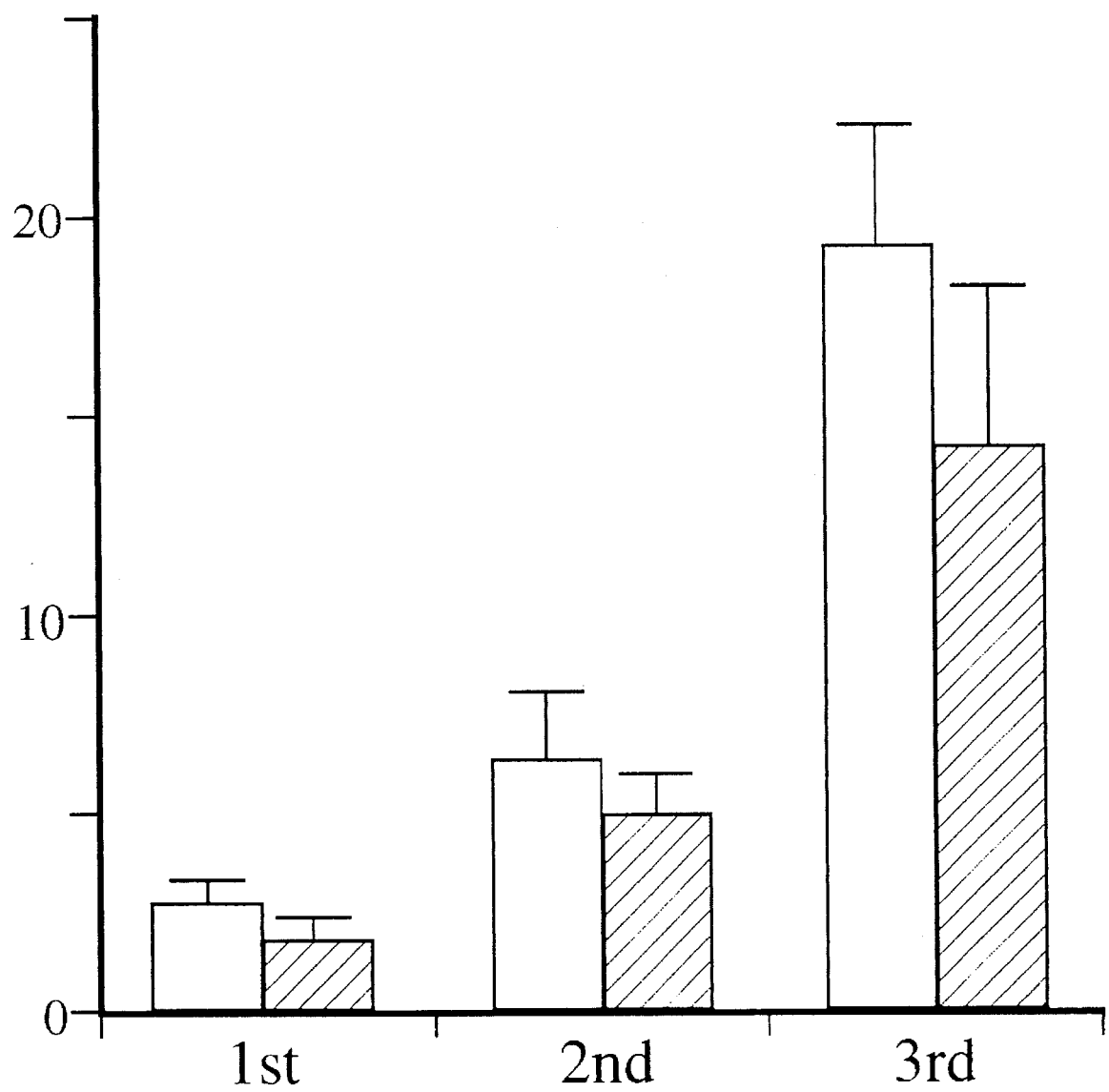

FIG. 4a demonstrates that the foreign MRP-A transcript partitions into mitochondria in parallel with endogenous MRP-RNA (FIG. 4b). Quantitative analysis (FIG. 4f) indicated that mitochondrial partitioning of the pMRP-A transcript was marginally lower than that of endogenous MRP-RNA, but this may not necessarily reflect less efficient mitochondrial import of the foreign gene product. It has been reported that transfection of cells in culture by calcium phosphate coprecipitation results in expression of foreign genes in less than 20% of the cell population (Sambrook et al., 1989).

Since foreign MRP-RNA transcripts were present in approximately equal abundance to the wild type transcripts in RNA extracted from the entire cell population, these results indicated that trans-gene expression was at least 5-fold greater than that of the endogenous gene within the fraction of cells that took up the plasmid DNA. Such high level expression in a small fraction of cells may saturate carriers in the import pathway and create the appearance of less efficient import.

Mitochondrial Partitioning of Deleted Forms of MRP-RNA

Using the same assay system, mitochondrial partitioning of deleted forms of MRP-RNA was examined. Transcripts derived from pMRP-B partitioned into mitochondria in a manner indistinguishable from pMRP-A and the endogenous gene product (FIG. 5), indicating that sequences from nt 181 to nt 255 are not involved in mitochondrial targeting. Although pMRP-D transfection resulted in a lower abundance of transcripts in the total cellular RNA pool, increasing gel loads and extending exposure time revealed that pMRP-D transcripts also partitioned similarly to pMRP-A, pMRP-B and endogenous MRP-RNA (FIG. 6). This indicated that the region from nt 6 to nt 115 also is not essential for identifying RNA for mitochondrial import.

In distinct contrast, the mutation present in transcripts derived from pMRP-F severely impaired its partitioning into mitochondria (FIG. 7). Although the pMRP-F transcripts accumulated to high levels within the cell, its fractionation pattern was similar to that of U1 RNA, indicating that removal of a 58 nucleotide region of RMR-RNA between nt 118 and 175 (SEQ ID NO: 9) rendered the resulting transcript defective for mitochondrial import.

FIG. 8 summarizes the results of this mutational analysis in terms of a standardized mitochondrial partition ratio. Transcripts from pMRP-A, pMRP-B and pMRP-D remained competent for mitochondrial import, while the mitochondrial partition ratio of MRP-F decreased by an order of magnitude.

Nuclear Partitioning of Mutant and Endogenous MRP-RNA

Following nuclear transcription, many mature RNAs reach the cytoplasm through controlled pathways through the nuclear envelope (Hamm and Mattaj, 1990; and reviewed by Nigg et al., 1991). The nuclear partitioning of mutant and endogenous MRP-RNAs was measured in order to determine if there was a blockade in the pathway out of the nucleus. Equal amounts of nuclear and total cellular RNA were probed with appropriate oligonucleotide probes. As shown in FIG. 9, all mutant MRP-RNAs partitioned to nuclei somewhat less efficiently than endogenous MRP-RNA. Nuclear partition ratios ranged from 0.28–0.42 (pMRP-A=0.28, pMRP-B=0.42, pMRP-D=0.41 and pMRP-F=0.32). These results suggested that carriers that stabilize MRP-RNA within the nuclear compartment, like those involved in mitochondrial import, may be saturable, so that transcripts accumulate preferentially in the cytoplasm when expression of heterologous MRP-RNA's is increased several fold above ambient levels. Additionally, the results indicated that defective mitochondrial import of MRP-F is not a result of failure of this transcript to exit from the nucleus.

EXAMPLE 2

The intracellular location of MRP-RNA was further supported by the results of in situ hybridization and electron microscopy studies on adult mouse myocardial cells. Cardiac myocytes manifest a high fractional volume of mitochondria and a high ratio of mtDNA to nuclear DNA, suggesting that if present, intramitochondrial MPR-RNA should be more readily detectably than in cells of lower respiratory activity. As shown in this example, MRP-RNA is preferentially localized both to nucleoli and to mitochondria in cardiomyocytes. These experiments therefore document mitochondrial partitioning of MRP-RNA by a method that avoids cell fractionation. This is important because of the virtually unavoidable contamination of purified mitochondrial fractions with small nuclear RNAs.

Localization of MRP-RNA to Nucleoli and Mitochrondia in Cardiomyocytes

In situ hybridization of an antisense $^{35}$S-labelled RNA probe to sections of adult mouse heart was analyzed by light microscopy and revealed prominent nuclear clustering of MRP-RNA within both cardiomyocytes and non-myocyte cells of the cardiac wall (not shown). This result was consistent with prior cell fractionation studies that localized the bulk of the intracellular pool of MRP-RNA to the nuclear pool of MRP-RNA to the nuclear compartment (Chang and Clayton, 1987). It was also found that hybridization of the antisense MRP-RNA probe within the cytoplasm exceeded that of an irrelevant RNA probe, suggesting that cardiomyocytes also contain a distinct cytoplasmic pool of MRP-RNA. Cytoplasmic binding of the antisense MRP-RNA probe was less apparent in non-muscle cells. The resolution obtainable by light microscopy was, however, insufficient to distinguish between intra-mitochondrial and extra-mitochondrial locations of cytoplasmic MRP-RNA.

Higher resolution was obtained by in situ hybridization using a biotinylated complementary RNA probe in ultrathin cryosections of adult mouse heart, followed by immunogold labeling and electron microcopy. Results are illustrated in FIG. 16, and show preferential binding of the antisense MRP-RNA probe to nucleoli and mitochondria.

The intracellular distribution of the antisense MRP-RNA probe and an irrelevant RNA control probe were determined quantitatively using a systematic random sampling technique (Gunderson and Jensen, 1987) by an experienced observer blinded to the identity of the probes. Results of a representative experiment employing this quantitative analysis are shown in FIG. 17. When results from three independent experiments were combined, binding of the antisense MRP-RNA signal to nucleoli and mitochondria was significantly greater than binding to myofibrils (Student's t test, p<.01). Hybrids formed between the antisense MRP-RNA probe and its cellular targets in nucleoli and mitochondria were resistant to RNAase H (not shown), indicating that the results were not confounded by hybridization of the antisense MRP-RNA probe to complementary sites in nuclear or mitochondrial DNA.

The presence of an authentic intramitochondrial pool of MRP-RNA indicated the existence of a pathway for mitochondrial import of RNA in mammalian cells and supports the involvement of RNAase MRP in intramitochondrial RNA processing and priming of mtDNA replication. The low abundance of MRP-RNA in mitochondrial factions from HeLa cells (Kiss and Filipowicz, 1992) may be attributable to the low respiratory activity of these cells in comparison to highly aerobic cells such as cardiomyocytes.

EXAMPLE 3

Although the exact role and function of MRP-RNA is not defined, the following experiments indicate one of many possible regulatory functions with respect to mtDNA replication and mitochondrial biogenesis. Expression of MRP-RNA in specialized subtypes of mammalian striated muscles was examined. The results showed that changes in abundance of MPR-RNA correlated with specific activity of citrate synthase, a marker of mitochondrial proliferation.

Induction of MRP-RNA by Contractile Activity in Striated Muscle

Animal Surgery and Tissue Preparation

Adult New Zealand White rabbits weighing 2.3–3.5 kg were anesthetized by isoflurane inhalation. Under sterile conditions, pulse generations were implanted and their electrodes placed adjacent to the common peroneal nerve of one hind limb according to the procedure described originally by Salmons and Vrbova (1969). Nerves were stimulated continuously at 6–10 Hz for 1, 3, 7, 14, or 21 days. The rabbits were anesthetized with pentobarbital sodium (50 mg/kg, iv) for removal of muscles under sterile conditions. Muscle tissue was rinsed in cold sterile saline, frozen in liquid nitrogen, and stored at −80° C. All protocols were reviewed and approved by the Institutional Review Board for Animal Research and were conducted in accordance with the *NIH Guide for the Care and Use of Laboratory Animals*.

Enzyme Assays

Citrate synthase activity was measured in whole muscle homogenates as described previously (Williams et al., 1986). Activities were expressed relative to muscle wet weight.

RNA Analysis

Total RNA was extracted from tissue samples by homogenization with guanidine isothiocyanate and centrifugation through 5.7M cesium chloride, followed by phenol-chloroform extraction and ethanol precipitation. RNA concentrations were measured spectrophotometrically from absorbance measurements made at 260 nm. Northern blots of total RNA were prepared on MagnaGraph Nylon Transfer Membranes by capillary blotting following electrophoresis in formaldehyde-agarose gels. RNA was immobilized by photocrosslinking (Stratolinker). Blots were prehybridized at 60° C. for 2–3 hours in 0.25M sodium phosphate (pH 7.2), 1 mM EDTA, 0.25M sodium chloride, 10% polyethylene glycol, 7% SDS, 1% bovine serum albumin, and 120 µg/ml of denatured salmon sperm DNA.

Oligonucleotides

Oligonucleotides were synthesized based on the published sequences of the coding regions for mouse MRP-RNA (Chang and Clayton, 1989) and U1 snRNA (Carmo-Fonseca et al., 1991) and included the sequences GAGAATGAGCCCCGTGTGGTTG (SEQ ID NO: 6) and GGTCTAAACCCAGCTCACGTTC (SEQ ID NO: 7), respectively. The resulting oligonucleotides were end-labeled with [$^{32}$P] ATP by T4 kinase. Hybridizations were performed at 60° C. for 16–24 hours in a shaking water bath. Filters were washed in 0.5× SSC, 0.1% SDS for 15 minutes twice at room temperature (MRP) or for 15 minutes twice at room temperature and 15 minutes twice at 40° C. (U1). The filters were placed on film (Amersham Hyperfilm-MP) and exposed for 24–96 hours. Autoradiograms were scanned using a Molecular Dynamics 300A Computing Densitometer.

Promoter Analysis

The MRP-RNA gene was cloned by PCR amplification from mouse genomic DNA using primers based on the published sequence (Topper and Clayton, 1990). The MRP-RNA gene construct, pMRP-A, consisted of 273 bp of coding region, 700 bp of 5' flanking DNA and the 3' transcriptional termination sequence. A unique Bgl II site was engineered near the 3' terminus of the coding region using Bgl II linker PCR primers. Deletion mutants were generated by PCR primer-guided synthesis and by restriction at unique sites to remove selected segments of the MRP-RNA promoter and coding regions. All the constructs were cloned into pBluescript KS (Stratagene, La Jolla, Calif.) and verified by restriction mapping and sequencing.

Mouse C2C12 myoblast cells were grown in Dulbecco's modified Eagle's medium with 10% fetal calf serum, 5% chick embryo extract and 20 units/ml penicillin-streptomycin. Calcium phosphate transfections were performed as described previously (Li et al., 1990). Thirty micrograms of plasmid DNA were added to each 100-mm dish. After two days, the duplicate plates of transfected cells were mixed. One half was used to extract transfected plasmid (Hirt, B., 1967) as a control for the efficiency of transfection, and the other half was employed for RNA isolation and Northern blot hybridization. The probe for these experiments was a synthetic oligonucleotide with sequence GAATGAGATCT-GTGGTTGGTGCG (SEQ ID NO: 4), end labelled with [$^{32}$P] ATP. This probe is complementary to transcripts derived from plasmid constructions that contain the BglII linker within the MRP-RNA coding region (pMRP-A and derivatives), but fails to hybridize to endogenous MRP-RNA

Effects of Nerve Stimulation on Citrate Synthase Activity

Continuous electrical stimulation of the motor nerve at 6–10 Hz led to increases in specific activity of citrate synthase in tibialis anterior muscles that were detectable by 7 days (1.5-fold over contralateral control muscles) and progressive up to 21 days (3.5-fold increase) of motor nerve stimulation (FIG. 12). These results were similar to those of extensive prior studies using this model (Henriksson et al., 1986; Seedorf et al., 1986; Williams et al., 1986; Williams R. S., 1986; Annex et al., 1991).

Effects of Nerve Stimulation on U1 and MRP-RNA

As shown in FIG. 13, expression of both U1 and MRP-RNA was induced within the first day of motor nerve stimulation. Longer periods of stimulation further increased the abundance of MRP-RNA, which peaked at levels approximately 14-fold greater than those seen in contralateral unstimulated muscles after 14 days of stimulation. By 21 days, MRP-RNA remained elevated (3.5-fold) above levels present in contralateral muscles, but declined from the apogee noted at earlier time points. Part of this late decline in stimulation-induced abundance of MRP-RNA between days 14 and 21 was attributable to small but consistent increases in MRP-RNA levels in contralateral unstimulated muscles in comparison to muscles from naive animals.

By contrast, the early induction of U1 snRNA was not sustained, and expression of U1 snRNA was maintained at levels approximately 1.5 times those seen in contralateral unstimulated muscles throughout the 21-day period of nerve stimulation. Like MRP-RNA, small but consistent increases in U1 snRNA were observed in contralateral unstimulated muscles of animals undergoing nerve stimulation for extended periods in comparison to naive animals.

The apparent increases in U1 and MRP-RNA in contralateral, unstimulated muscles between days 14 and 21 could be attributable to any of several factors, including: variations among those non-inbred animals in basal expression of small RNAs; recovery from stress-induced depression of basal expression of these small RNAs associated with the surgical procedure; systemic effects of chronic nerve stimulation on unstimulated muscles. The basis for these variations in expression of U1 and MRP-RNA among control muscles is immaterial in the described experiments in which each animal serves as its own control.

Relative Abundance of MRP-RNA in Specialized Muscle Subtypes

MRP-RNA was expressed to higher levels in mitochondria-rich cardiac and slow skeletal muscles than in glycolytic fast skeletal muscles of adult rabbits (FIG. 14). These results complement the analysis of effects of nerve stimulation and suggest a consistent relationship between respiratory activity and expression of MRP-RNA among striated muscles of this species.

Promoter Analysis

The pMRP-A construct that includes the proximal 700 bp of 5' flanking region and coding region of the mouse MRP-RNA gene was expressed to high levels following transfection into C2C12 myogenic cells (FIG. 15A). Efficient transcription in this cell background was independent of intragenic sequences, including a motif similar to the Box A elements of tRNA genes, as determined by the continued high expression of constructs with internal deletions collectively spanning more than 90% of the coding region. Likewise, sequences upstream of position −223, relative to the transcriptional start site, appeared to be dispensable for transcription in this transient expression system. By contrast, when removed either by 5' or internal deletions, sequences between −223 and −84 were essential for promoter activity (FIG. 15C). Variations in expression of the reporter gene (MRP-RNA carrying the BglII linker) were not attributable to differences in efficiency of transfection, as assessed by recovery of plasmid constructs from transfected cells (FIG. 15B).

EXAMPLE 4

The region between nt 118 and nt 175 (SEQ ID NO: 9) of mouse MRP-RNA was analyzed by an algorithm to determine features of secondary structure. A stable stem-loop was found to be preserved in all forms of MRP-RNA efficiently imported into mitochondria.

Secondary Structure of Mouse MRP-RNA

Analysis of the nt 118 to nt 175 (SEQ ID NO: 9) region of mouse MRP-RNA was made using an algorithm to predict secondary structure.

REFERENCE AND BRIEF DETAILS OF HOW USED

The nt 118–175 region (SEQ ID NO: 9) contained an evolutionarily conserved sequence (nt 144 to nt 156) within a flexible base-pairing region, as well as a stable stem-loop (FIG. 10). This was preserved in all of the forms of MRP-RNA that were efficiently imported into mitochondria.

EXAMPLE 5

A simplified model, illustrated in FIG. 11, is consistent with the data concerning the intracellular trafficking of MRP-RNA. The impaired mitochondrial partitioning of pMRP-F may be attributable to failure of its transcript to be recognized by a protein carrier(s) of a mitochondrial import apparatus. Transcripts of pMRP-D are likely to be labile due to defective binding to a protein(s) that stabilize the transcript within the nuclear compartment (possibly To/Th antigen).

While the compositions and methods of this invention have been described in terms of preferred embodiments, it will be apparent to those of skill in the art that variations may be applied to the methods, compositions, and in the steps or sequences of steps of the methods described herein without departing from the concept, scope and spirit of the invention. More specifically, it will be apparent that certain agents which are biologically or physiologically related may be substituted for the for the agents described herein with the same or similar results achieved. All such similar substitutes and modifications apparent to those skilled in the art are deemed to be within the scope, spirit and concept of the invention as defined by the appended claims.

REFERENCES

The references listed below are incorporated herein by reference to the extent they supplement, explain, provide a background for or teach methodology, techniques and/or compositions employed herein.

Anderson, S., Bankier, A. T., Barrell, B. G., de Bruijn, M. H. L., Coulson, A. R., Drouin, J., Eperon, I. C., Nierlich, D. P., Roe, B. A., Sanger, F., Schreier, P. H., Smith, A. J. H., Staden, R., and Young, IlG. (1981). Sequence and organization of the human mitochondrial Genome. *Nature* 290, 457–465.

Annex, B. H., Kraus, W. E., Dohm, G. L., and Williams, R. S., (1991). *Am. J. Physiol.* 260, C266–C270.

Annex, B. H., and Williams, R. S., (1990). Mitochondrial DNA structure and expression in specialized subtypes of mammalian striated muscles. *Mol. Cell. Biol.* 10, 5671–5678.

Aquila, H., Link, T. A., and Klingenberg, M. (1987). Solute carriers involved in energy transfer of mitochondria form a homologous protein family. *FEBS Letters* 212, 1–9.

Attardi, G., and Schatz, G. (1988). Biogenesis of mitochondria. *Ann. Rev. Cell Biol.* 4, 289–333.

Bennett, J. L., and Clayton, D. A. (1990). Efficient site-specific cleavage by RNase MRP requires interaction with two evolutionarily conserved mitochondrial RNA sequences. *Mol. Cell. Biol.* 10, 2191–2201.

Bibb, M. J., Van Etten, R. A., Wright, C. T., Walberg, M. W., and Clayton, D. A. (1981). Sequence and gene organization of mouse mitochondrial DNA. *Cell* 26, 167–180.

Bogenhagen, D. F., Sakonju, S., and Brown, D. D. (1980). A control region in the center of the 5S RNA gene directs specific initiation of transcription: II. The 3' border of the region. *Cell* 19, 27–35.

Carbon, P., Murgo, S., Ebel, J. P., Krol, A., Tebb, G., and Mattaj, I. M. (1987). A common octamer motif binding protein is involved in the transcription of U6 snRNA polymerase III and U2 snRNA polymerase II. *Cell* 51, 71–79.

Carmo-Fonseca, M., Tollervey, D., Pepperkok, R., Barabino, S. M. L., Merdes, A., Brunner, C., Zamore, P. D., Green, M. R., Hurt, E., and Lamond, I. (1991). Mammalian nuclei contain foci which are highly enriched in components of the pre mRNA splicing machinery. *EMBO J.* 10, 195–206.

Chang, D. D., and Clayton, D. A., (1987a). A novel endoribonuclease cleaves at a priming site of mouse mitochondrial DNA replication. *EMBO J.* 6, 409–417.

Chang, D. D., and Clayton, D. A., (1987b). A mammalian mitochondrial RNA processing activity contains nucleus-encoded RNA. *Science* 235, 1178–1184.

Chang, D. D., and Clayton, D. A., (1989). Mouse RNAase MRP RNA is encoded by a nuclear gene and contains a decamer sequence complementary to a conserved region of mitochondrial RNA substrate. *Cell* 56, 131–139.

Chomyn, A., Meola, G., Bresolin, N., Lai, S. T., Scarlato, G., and Attardi, G. (1991). In vitro genetic transfer of protein synthesis and respiration defects to mitochondrial DNA-less cells with myopathy-patient mitochondria. *Mol. Cell. Biol.* 11, 2236–2244.

Clayton, D. A. (1991). Nuclear gadgets in mitochondrial DNA replication and transcription. *Trends in Biochem. Sci.* 107–111.

Das, G., Henning, D., Wright, D., and Reddy, Ram. (1988). Upstream regulatory elements are necessary and sufficient for transcription of a U6 RNA gene by RNA polymerase III. *EMBO J.* 7, 503–512.

Dignam, J. D., Lebowitz, R. M., and Roeder, R. C. (1983). Accurate transcription initiation by polymerase II in a soluble extract from isolated mammalian nuclei. *Nucleic Acid Res.* 11, 1475–1489.

Doersen, C. J., Guerrier-Takada, C., Altman, S., and Attardi, G. (1985). Characterization of an RNase P activity from Hela cell mitochondria, comparison with the cytosol RNase P activity. *J. Biol. Chem.* 260, 5942–5949.

Ellis, R. J. and van der Vies, S. M., (1991) Molecular Chaperones. *Ann. Rev. Biochem.* 60, 321–327.

Evans, M. J. and Scarpulla, R. C. (1989). *J. Biol. Chem.* 264, 14361–14368.

Galli, G., Hofstetter, H., and Birnstiel, M. L. (1981). Two conserved sequence blocks within eucaryotic tRNA genes are major promoter elements. *Nature* 294, 626–631.

Gold, H. A., Topper, J. N., Clayton, D. A., and Craft, J. (1989). The RNA processing enzyme RNase MRP is identical to the Th RNP and related to RNase P. *Science* 245, 1377–1380.

Goto, Y., Nonaka, I., and Horai, S. (1990). A mutation in the tRNA$^{Leu(UUR)}$ gene associated with the MELAS subgroup of mitochondrial encephalomyopathies. *Nature* 348, 651–653.

Grossman (1990). *American Journal Human Genetics* 46, 415–417.

Gundersen, H. J. G., and Jensen, E. B. (1987). The efficiency of systematic sampling in stereology and its prediction. *J. Microsc.* 147, 229–263.

Hamm, J., and Mattaj, I. W. (1990). Monomethylated cap structures facilitate RNA export from the nucleus. *Cell* 63, 109–118.

Hattori et al. (1991). *American Heart Journal* 1735–1742.

Henriksson, J., Chji, M. M.-Y., Hintz, C. S., Young, D. A., Kaiser, K. K., Salmons, S., and Lowry, O. H. (1986). *Am. J. Physiol.* 251, C614–C632.

Hirt, B. (1967). Selective extraction of polyoma DNA from infected mouse culture. *J. Mol. Biol.* 26, 365–369.

Hofstetter, H., Kressmann, A., and Birnstiel, M. L. (1981). A split promoter for a eucaryotic tRNA gene. *Cell* 24, 573–585.

Holt, I. J., Harding, A. E., and Morgan-Hughes, J. A. (1988). Deletions of muscle mitochondrial DNA in patients with mitochondrial myopathies. *Nature* 331, 717–719.

Hood, D. A., Zak, A. R., and Pette, D. (1989). *Eur. J. Biochem.* 179, 275–280.

Howell, N., Nalty, M. S., and Appel, J. (1986). A digitonin-based procedure for the isolation of mitochondrial DNA from mammalian cells. *Plasmid* 16, 77–80.

Karwan, R., Bennett, J. L., and Clayton, D. A. (1991). Nuclear RNase MRP processes RNA at multiple discrete sites: interaction with an upstream G box is required for subsequent downstream cleavages. *Genes & Development* 5, 1264–1276.

Kiss, T., and Filipowicz, W. (1992). Evidence against a mitochondrial location of the 7-2/RMP RNA in mammalian cells. *Cell* 70, 11–16.

Kruse, B., Narasimhan, N., and Attardi, G. (1989). Termination of transcription in human mitochondria: identification and purification of a DNA binding protein factor that promotes termination. *Cell* 58, 391–397.

Kunkel, G. R., and Peterson, T. (1988). Upstream elements required for efficient transcription of a human U6 RNA gene resemble those of U1 and U2 genes even though a different polymerase is used. *Genes Development* 2, 196–204.

Lander, E. S., and Lodish, H. (1990). Mitochondrial diseases: gene mapping and gene therapy. *Cell* 61, 925–926.

Li, K., Hodge, J. A., and Wallace, D. C. (1990). OXBOX, a positive transcriptional element of the heart-skeletal muscle ADP/ATP translocator gene. *J. Biol. Chem.* 265, 20585–20588.

Manning-Krieg, U. C., Scherer, P. E., and Schats, G. (1991). Sequential action of mitochondrial chaperones in protein import into the matrix. *EMBO J.* 10, 3273–3280.

Mottram, J. C., Bell, S. D., Nelson, R. G., and Barry, J. D. (1991). tRNAs of trypanosoma brucet, unusual gene organization and mitochondrial importation. *J. Biol. Chem.* 266, 18313–18317.

Moreadith, R. W., and Fiskum, G. (1984). Isolation of mitochondria from ascites tumor cells permeabilized with digitonin. *Analytical Biochem.* 137, 360–367.

Murphy, S., Liegro, C. D., and Melli, M. (1987). The in vitro transcription of the 7SK RNA gene by RNA polymerase III is dependent only on the presence of an upstream promoter. *Cell* 51, 81–87.

Nagley, P. (1989). Trafficking in small mitochondrial RNA molecules. *Trend in Genet* 5, 67–69.

Nigg, E. A., Baeuerle, P. A., and Luhrmann, R. (1991). Nuclear import-export: in search of signals and mechanisms. *Cell* 66, 15–22.

Overhauser, J., McMahan, J., and Wasmuth, J. J. (1987). Identification of 28 DNA fragments that detect RFLPs in 13 distinct physical regions of the short arm of chromosome 5. *Nucleic Acid Res.* 15, 4617–4627.

Parisi, M., and Clayton, D. A. (1991). Similarity of human mitochondrial transcription factor 1 to high mobility group proteins. *Science* 252, 965–969.

Parsons, W. J., Richardson, J. A., Graves, K. A., Williams, R. S., and Moreadith, R. W. (1993). Gradients of transgene expression directed by the human myoglobin promoter in the developing mouse heart. *Proc. Natl. Acad. Sci. U.S.A.* (in press)

Picard, B., and Wegnez, M. (1979). Isolation of a 7S particle from Xenopus laevis oocytes: A 5S RNA-protein complex. *Proc. Natl. Acad. Sci. USA* 76, 241–245.

Reimer, G., Raska, I., Scheer, U., and Tan, E. M. (1988). Immunolocalization of 7-2-Ribonucleoprotein in the granular component of the nucleolus. *Exp. Cell Res.* 176, 117–128.

Sakonju, S., Bogenhagen, D. F., and Brown, D. D. (1980). A control region in the center of the 5s RNA gene directs specific initiation of transcription: 1. The 5' border of the region. *Cell* 19, 13–25.

Salmons, S. and Vrbova, G. (1969). *J. Physiol. (Lond.)* 201, 535–549.

Sambrook, J., Fritsch, E. F., and Maniatis, T. (1989). Molecular cloning, a laboratory manual. Cold Spring Harbor Lab. Press, Cold Spring Harbor, N.Y., pp. 7.19–7.22; pp. 16.30–16.32.

Seedorf, U., Leberer, E., Kirschbaum, B. J., and Pette, D. (1986). *Biochem. J.* 239, 115–120.

Shoffner, J. M., Lott, M. T., Lezza, A. M. S., Seibel, P., Ballinger, S., and Wallace, D. C. (1990). Myoclonic epilepsy and ragged-red fiber disease (MERRF) is associated with a mitochondrial DNA tRNA$^{Lys}$ mutation. *Cell* 61, 931–937.

Sollner, T., Rassow, J., Wiedmann, M., Schlossmann, J., Keil, P., and Neupert, W. (1991). Mapping of the protein import machinery in the mitochondrial outer membrane by crosslinking of translocation intermediates. *Nature* 355, 84–87.

Topper, J. N., Bennett, J. L., and Clayton, D. A. (1992). A role for RNAase MRP in mitochondrial RNA processing. *Cell* 70, 16–20.

Topper, J. N., and Clayton, D. A. (1990a). Secondary structure of the RNA component of a nuclear/mitochondrial ribonucleoprotein. *J. Biol. Chem.* 265, 13254–13262.

Topper, J. N., and Clayton, D. A. (1990b). Characterization of human MRP/Th RNA and its nuclear gene: full length MRP/Th RNA is an active endoribonuclease when assembled as an RNP. *Nucleic Acids Res.* 18, 793–799.

Ullu, E., and Weiner, A. (1984). Human genes and pseudogenes for the 7SL RNA component of signal recognition particle. *EMBO J.* 3, 3303–3310.

Ullu, E., and Weiner, A. (1985). Upstream sequences modulate the internal promoter of the human 7SL RNA gene. *Nature* 318, 371–374.

Vestweber, D., and Schatz, G. (1989). DNA-protein conjugates can enter mitochondria via the protein import pathway. *Nature* 338, 170–172.

Waldschmidt, R., Wanandi, I., and Seifart, K. H. (1991). Identification of transcription factors required for the expression of mammalian U6 genes in vitro. *EMBO J.* 10, 2595–2603.

Wallace, D. C., Singh, G., Lott, M. T., Hodge, J. A., Schurr, T. G., Lezza, A. M. S., Elsas, L. J., and Nikoskelainene, E. K. (1988). Mitochondrial DNA mutation associated with Leber's hereditary optic neuropathy. *Science* 242, 1427–1430.

Williams, R. S. (1986). Mitochondrial gene expression in mammalian striated muscle: Evidence that variation in gene dosage is the major regulatory event. *J. Biol. Chem.* 261, 12390–12394.

Williams, R. S., Garcia-Moll, M., Mellor, J., Salmons, S., and Harlan, W. (1987). *J. Biol. Chem.* 262, 2764–2767.

Williams, R. S., Salmons, S. Newsholme, E. A., Kaufman, R. E., and Mellor, J. (1986). *J. Biol. Chem.* 261, 376–380.

Yuan, Y., Singh, R., and Reddy, R. (1989). Rat nucleolar 7-2 RNA is homologous to mouse mitochondrial RNase mitochondrial RNA-processing RNA. *J. Biol. Chem.* 264, 14835–14839.

Yuan, Y., Tan, E., and Reddy, R. (1991). The 40-kilodalton to autoantigen associates with nucleotides 21 to 64 of human mitochondrial RNA processing/7-2 RNA in vitro. *Mol. Cell. Biol.* 11, 5266–5274.

Yuan, Y., and Reddy, R. (1991). 5' flanking sequences of human MRP/7-2 RNA gene are required and sufficient for the transcription by RNA polymerase III. *Biochem. Biophys. Acta* 1089, 33–39.

Zuker, M., and Stiegler, P. (1981). Optimal computer folding for large RNA sequence using thermodynamics and auxiliary information. *Nucleic Acid Res.* 9, 133–148.

---

What is claimed is:

1. An isolated RNA encoded within the midportion of mammalian mitochondrial RNA-processing endoribonuclease RNA gene consisting of a coding region that imports into mitochondria but lacks transcriptional control elements selected from the group consisting of SEQ I.D. NOs. 1, 8, and 9.

2. The isolated RNA of claim 1 which has the sequence of SEQ ID NO. 1 or SEQ ID NO: 8.

3. The isolated RNA of claim 1 wherein the midportion of the mammalian MRP-RNA gene consisting of 58 base pairs of coding region nt118 to 175, SEQ ID NO: 9.

4. A DNA segment which is fully complementary to any of the RNA of claims 1–3.

5. A recombinant vector comprising the DNA consisting of claim 4.

6. A recombinant cell transformed with the recombinant vector of claim 5.

7. The recombinant cell of claim 6 which is a eukaryotic cell.

8. The recombinant cell of claim 6 which is a myoblast cell.

* * * * *